(12) United States Patent
Davenport et al.

(10) Patent No.: US 9,708,622 B2
(45) Date of Patent: Jul. 18, 2017

(54) TRANSGENIC PLANTS WITH ALTERED NITRATE LEVELS IN LEAVES

(71) Applicant: BRITISH AMERICAN TOBACCO (INVESTMENTS) LIMITED, London (GB)

(72) Inventors: Susan Davenport, London (GB); Pascaline Le Lay, London (GB); Juan Pablo Sanchez Tamburinno, London (GB)

(73) Assignee: British American Tobacco (Investments) Limited, London (GB)

( * ) Notice: Subject to any disclaimer, the term of this patent is extended or adjusted under 35 U.S.C. 154(b) by 95 days.

(21) Appl. No.: 14/386,719

(22) PCT Filed: Mar. 19, 2013

(86) PCT No.: PCT/GB2013/050708
§ 371 (c)(1),
(2) Date: Sep. 19, 2014

(87) PCT Pub. No.: WO2013/140155
PCT Pub. Date: Sep. 26, 2013

(65) Prior Publication Data
US 2015/0075548 A1 Mar. 19, 2015

(30) Foreign Application Priority Data
Mar. 20, 2012 (GB) .................................. 1204869.0

(51) Int. Cl.
*A01H 1/00* (2006.01)
*A01H 5/12* (2006.01)
*C12N 15/82* (2006.01)
*C07K 14/415* (2006.01)
*A24B 13/00* (2006.01)
*A24D 1/00* (2006.01)
*C12N 15/00* (2006.01)

(52) U.S. Cl.
CPC .......... *C12N 15/8243* (2013.01); *A24B 13/00* (2013.01); *A24D 1/00* (2013.01); *C07K 14/415* (2013.01); *C12N 15/8216* (2013.01); *C12N 15/8251* (2013.01)

(58) Field of Classification Search
None
See application file for complete search history.

(56) References Cited

U.S. PATENT DOCUMENTS

| | | | |
|---|---|---|---|
| 7,329,797 B2 * | 2/2008 | Schneeberger | C12N 15/8242 435/320.1 |
| 2006/0143736 A1 * | 6/2006 | Schneeberger | C12N 15/8242 800/284 |
| 2007/0044172 A1 | 2/2007 | Schneeberger et al. | |
| 2010/0162432 A1 | 6/2010 | Puzio et al. | |
| 2011/0010797 A1 | 1/2011 | Tsay et al. | |
| 2011/0239324 A1 | 9/2011 | Davenport et al. | |

FOREIGN PATENT DOCUMENTS

| | | |
|---|---|---|
| EP | 0116718 A1 | 8/1984 |
| EP | 0242246 A1 | 10/1987 |
| EP | 0249637 A1 | 12/1987 |
| EP | 0270822 A1 | 6/1988 |
| EP | 0369637 A2 | 5/1990 |
| GB | 2197653 A | 5/1988 |
| WO | 87/03659 A1 | 6/1987 |
| WO | 0039300 A1 | 7/2000 |
| WO | 2004007730 A1 | 1/2004 |
| WO | 2006/062971 A2 | 6/2006 |
| WO | 2009105492 A2 | 8/2009 |
| WO | 2012/038717 A1 | 3/2012 |

OTHER PUBLICATIONS

Bevan, M.: "Binary Agrobacterium vectors for plant transformation", Nucleic Acids Research, 1984, vol. 12, No. 22, pp. 8711-8721.

Chopin F. et al.: "The Arabidopsis ATNRT2.7 Nitrate Transporter Controls Nitrate Content in Seeds", The Plant Cell, May 2007, vol. 19, No. 5, pp. 1590-1602, XP002609921.

Cornejo, M.-J. et al.: "Activity of a maize ubiquitin promoter in transgenic rice", Plant Molecular Biology, 1993, vol. 23, pp. 567-581.

Diaz C. et al.: "Characterization of Markers to Determine the Extent and Variability of Leaf Senescence in Arabidopsis. A Metabolic Profiling Approach", Plant Physiology, Jun. 2005, vol. 138, pp. 898-908.

Horsch R. B. et al.: "A Simple and General Method for Transferring Genes into Plants", Biological Sciences, Mar. 8, 1985, vol. 227, pp. 1229-1231.

Kuluev B. R. et al.: "Activity of Promoters of Carnation Etched Ring Virus and Dahlia Mosaic Virus in Tobacco Protoplasts and Transgenic Plants", Russian Journal of Plant Physiology, 2008, vol. 55, No. 5, pp. 687-693.

Masclaux C. et al.: "Characterization of the sink/source transition in tobacco (*Nicotiana tabacum* L.) shoots in relation to nitrogen management and leaf senescence", Planta, 2000, vol. 211, pp. 510-518.

(Continued)

*Primary Examiner* — Phuong Bui
(74) *Attorney, Agent, or Firm* — McKee, Voorhees & Sease, PLC

(57) ABSTRACT

The present invention relates to genetic constructs, which can be used in the preparation of transgenic plants. The constructs can have the ability of reducing nitrate concentration in the plant, in particular the plant's leaves, and for inducing a senescence-like phenotype. The invention extends to plant cells transformed with such constructs, and to the transgenic plants themselves. The invention also relates to methods of producing transgenic plants, and to methods of reducing nitrate content in plants. The invention also relates to harvested plant leaves, for example tobacco leaves, that have been transformed with the genetic constructs, and to various tobacco articles, such as smoking articles, comprising such harvested plant leaves.

10 Claims, 8 Drawing Sheets

(56) References Cited

OTHER PUBLICATIONS

Matt, P. et al.: "The immediate cause of the diurnal changes of nitrogen metabolism in leaves of nitrate-replete tobacco: a major imbalance between the rate of nitrate reduction and the rates of nitrate uptake and ammonium metabolism during the first part of the light period", Plant, Cell and Environment, 2001, vol. 24, No. 2, pp. 177-190.
Okamoto M. et al.: "Regulation of NRT1 and NRT2 Gene Families of Arabidopsis thaliana: Responses to Nitrate Provision", Plant and Cell Physiology, 2003, vol. 44, No. 3, pp. 304-317.
Hull, R. et al.: "The sequence of carnation etched ring virus DNA: comparison with cauliflower mosaic virus and retroviruses", The EMBO Journal, 1986, vol. 5, No. 12, pp. 3083-3090.
Seebauer J. R. et al.: "Amino Acid Metabolism in Maize Earshoots. Implications for Assimilate Preconditioning and Nitrogen Signaling", Plant Physiology, Dec. 2004, vol. 136, No. 4, pp. 4326-4334.
Sharma, A. et al.: "Determination of nitric oxide metabolites, nitrate and nitrite, in Anopheles culicifacies mosquito midgut and haemolymph by anion exchange high-performance liquid chromatography: plausible mechanism of refractoriness", Malaria Journal, 2008, vol. 7:71.
Thompson J. D. et al.: "CLUSTAL W: improving the sensitivity of progressive multiple sequence alignment through sequence weighting, position-specific gap penalties and weight matrix choice", Nucleic Acids Research, 1994, vol. 22, No. 22, pp. 4673-4680.
Thompson J. D. et al.: "The CLUSTAL_X windows interface: flexible strategies for multiple sequence alignment aided by quality analysis tools", Nucleic Acids Research, 1997, vol. 25, No. 24, pp. 4876-4882.
van Engelen F. A. et al.: "pBINPLUS: an improved plant transformation vector based on pBIN19", Transgenic Research, 1995, vol. 4, pp. 288-290.
Zhang W. et al.: "Analysis of rice Act1 5' Region Activity in Transgenic Rice Plants", The Plant Cell, Nov. 1991, vol. 3, pp. 1155-1165.
Database UniProt [Online], Oct. 1, 2000, "RecName: Full=High affinity nitrate transporter 2.5; Short=AtNRT2:5", XP002699717.
International Search Report and Written Opinion, mailed Jul. 10, 2013, for PCT/GB2013/050708.
Written Opinion of the International Preliminary Examining Authority, mailed Mar. 10, 2014, for PCT/GB2013/050708.
International Preliminary Report on Patentability, mailed on Jun. 30, 2014, for PCT/GB2013/050708.
Morcuende R et al., "Sucrose-feeding leads to increase rates of nitrate assimilation, increased rates of alpha-oxoglutarate synthesis, and increased synthesis of a wide spectrum of amina acids in tobacco leaves", PLANTA, vol. 206, No. 3, pp. 394-409.
Chiu, Chi-Chou, et al. "Mutation of a Nitrate Transporter, AtNRT1:4, Results in a Reduced Petiole Nitrate Content and Altered Leaf Development" Plant Cell Physiol. (2004) 45(9): pp. 1139-1148.

\* cited by examiner pGNP024 0096 001 (T1264) map

TRANSGENIC PLANTS WITH ALTERED NITRATE LEVELS IN LEAVES

CROSS-REFERENCE TO RELATED APPLICATIONS

This application is the National Stage of International Patent Application Serial No. PCT/GB2013/050708, filed Mar. 19, 2013, which claims priority to and the benefits of Great British Patent Application Serial No. 1204869.0 filed Mar. 20, 2012, each of which is herein incorporated by reference in its entirety for all purposes.

TECHNICAL FIELD

The present invention relates to genetic constructs, which can be used in the preparation of transgenic plants. The constructs can have the ability of reducing nitrate concentration in the plant, in particular the plant's leaves. The invention extends to plant cells transformed with such constructs, and to the transgenic plants themselves. The invention also relates to methods of producing transgenic plants, and to methods of reducing nitrate content in plants. The invention also provides methods for modifying plant amino acid profiles. The invention also relates to harvested plant leaves, for example tobacco leaves, that have been transformed with the genetic constructs, and to various tobacco articles, such as smoking articles, comprising such harvested plant leaves.

BACKGROUND

Nitrogen assimilation is of fundamental importance to the growth of plants. Of all the mineral nutrients required by plants, nitrogen is required in the greatest abundance. The main forms of nitrogen taken up by plants in the field are nitrate and ammonia, the principle components of nitrogenous fertilizers. Plants take up either nitrate or ammonium ions from the soil, depending on availability. Nitrate will be more abundant in well-oxygenated, non-acidic soils, whilst ammonium will predominate in acidic or water-logged soils. Experiments on growth parameters of tobacco clearly demonstrated that relative growth rate, chlorophyll content, leaf area and root area increased dramatically in response to increasing nitrate supply.

Plants have developed a very efficient nitrogen uptake system in order to cope with the large variation in nitrate content of cultivated soils. Plant roots take up nitrate and ammonia by the action of specific nitrate transporters (NTR). Two nitrate transport systems have been shown to coexist in plants, the NRT1 gene family and the NRT2 gene family. It is believed that both transporter families act cooperatively to take up nitrate from soil and distribute it around plants. It is generally assumed that the NRT1 gene family mediates the root low-affinity transport system (LATS, i.e. when external nitrate concentration >1 mM), while the NRT2 gene family mediates the high affinity transport system (HATS, i.e. when external nitrate concentration <1 mM). In *Arabidopsis*, seven genes are known to belong to the NRT2 gene family. It is also known that expression of these genes is regulated by the concentration of nitrate to which a plant is exposed.

However, excluding Atnrt2.1, Atnrt2.4 and Atnrt2.7, the function of the other NRT2 genes has not been elucidated.

One of the best characterized members of the NRT2 gene family is Atnrt2.1. AtNRT2.1 interacts with NAR2 (AtNRT3) protein to form a major component of the HATS in *Arabidopsis*. Over-expression of a mutated, non-functional form of the AtNRT2.1 nitrate transporter protein in *Arabidopsis* causes a significant reduction in the activity of the high-affinity nitrate-uptake system and a reduction in leaf nitrate content. As a consequence, the growth of these Nrt2.1 mutant plants was severely impaired when *Arabidopsis* was grown in low nitrate concentrations.

Nrt2.7 is a poorly characterized gene. It is known to be expressed in plant seeds, specifically in the vacuolar membrane, and it regulates the nitrate content of plant seeds. The nitrate transporter Nrt2.4 has been recently characterized. The NRT2.4 protein is involved in the uptake of nitrate by the roots of plants, at very low external concentrations, and in the loading of nitrates into the phloem of plant shoots.

The regulation of the activities of nitrate transporters, and nitrate and nitrite reductases is critical in controlling primary nitrogen assimilation throughout the plant, and has a significant impact on the growth and development of the plant. However, under certain conditions, nitrate may accumulate, mainly in green photosynthetically active tissues, where it is stored in the vacuoles of the mesophyll cells. High levels of nitrate accumulation can occur during periods of low temperature and/or solar irradiation (for example, in greenhouse crops during the winter), when there is less photosynthetic capacity to assimilate the stored nitrate, or as a result of high nitrate levels in the soil.

An increase in nitrate levels can have a number of deleterious consequences, not only in terms of plant growth, but also in terms of human or animal health where the plant is consumed, as well as environmental consequences. Many of the adverse consequences of nitrate accumulation are mediated through the production of nitrite.

Therefore, to prevent nitrate accumulation, one strategy would be increasing nitrogen remobilisation in plants, for example when they become senescent, which could have important applications in crop production. Firstly, nitrogen remobilised from leaves can be transported to the younger leaves as well as the developing seed. Increasing the efficiency of nitrogen exit from senescent leaves could therefore potentially increase nitrogen supply to seeds and younger parts of the plant, and thereby increase crop yield and nitrogen use efficiency. This is clearly a valuable goal when the world population is increasing but crop yields are not increasing sufficiently to meet demand. One potential target crop is *Brassica napus* (oilseed rape), which has poor nitrogen efficiency due to poor nitrogen remobilisation from vegetative tissue. Another target crop is wheat, as the potential benefits of increasing grain protein content are great. Grain protein content not only affects nutritive value of wheat, but also determines grain usage and therefore market value. For example, increased grain protein content results in increased bread volume.

Also, an ability to increase nitrogen remobilisation could be very useful in the tobacco industry because it is known that residual nitrogen in tobacco leaves contributes to the formation of nitrosamines, as illustrated in FIG. 1. In particular, nitrate and nitrite act as precursors to tobacco-specific nitrosamine (TSNA) formation in cured leaf. The processing of the tobacco leaves by the tobacco industry involves the removal of petioles and midribs of the cured leaves which are believed to act as nitrate storage organs, devoid of flavour and high in TSNAs.

Also, the formation of nitrosamines in the stomach is a result of endogenous nitrosation. Oral bacteria chemically reduce nitrate consumed in food and drink to nitrite, which can form nitrosating agents in the acidic environment of the stomach. These react with amines to produce nitrosamines and cause DNA strand breaks or cross linking of DNA. Another problem associated with an excess of nitrate is the formation of methaemoglobin which gives rise to blue baby syndrome, where the oxygen carrying capacity of haemoglobin is blocked by nitrite, causing chemical asphyxiation in infants.

As a consequence of these health concerns, a number of regulatory authorities have set limits on the amount of nitrate allowed in leafy green vegetables such as spinach and lettuce (e.g. European Commission Regulation 653/2003), depending on the time of harvest. These limits have resulted in any produce with a high nitrate content being unmarketable. Consequently, there have been efforts to reduce nitrate content of plants by managing the application of nitrogen-containing fertilisers or improved systems of crop husbandry. Some authorities have also set limits on the amounts of nitrate in drinking water.

There is therefore a need for means for alleviating the adverse effects associated with nitrate accumulation in plants. With this in mind, the inventors have developed a genetic construct, which may be used in the preparation of transgenic plants, which exhibits surprisingly reduced nitrate concentrations.

SUMMARY OF THE INVENTION

Thus, according to a first aspect of the invention, there is provided a genetic construct comprising a promoter operably linked to a coding sequence encoding a polypeptide having nitrate transporter activity, wherein the polypeptide comprises an amino acid sequence as set out in SEQ ID No. 3, or a functional variant or fragment or orthologue thereof, with the proviso that the promoter is not an SP6 promoter.

As described in the Examples, the inventors have investigated the remobilisation of nitrogen in a plant, with a view to developing plants which exhibit decreased concentrations of nitrate, especially in the leaves. The inventors have prepared a genetic construct (seen FIG. 2), in which a gene encoding a nitrate transporter protein was placed under the control of a promoter, which was not the SP6 promoter, such as a constitutive promoter or a tissue-specific promoter.

The coding sequence in the construct may encode the *Arabidopsis* nitrate transporter, AtNRT 2.5. The genomic DNA sequence (including introns and exons) encoding one embodiment of *Arabidopsis* nitrate transporter Nrt2.5 is provided herein as SEQ ID No. 1, as follows:

```
                                           [SEQ ID No. 1]
ATGGAGGTCGAAGGCAAAGGAGGAGAAGCTGGAACCACCACCACAACCGC

ACCTCGGAGGTTCGCACTTCCGGTGGACGCGGAGAACAAAGCAACAACTT

TCCGACTATTCTCAGTCGCTAAACCTCACATGAGAGCTTTCCATCTCTCA

TGGTTTCAATTCTTTTGCTGCTTCGTCTCCACTTTCGCAGCTCCGCCTCT

CCTCCCTGTTATCCGTGAAAATCTTAACCTCACCGCCACCGACATCGGAA

ACGCCGGAATAGCCTCTGTCTCCGGCGCTGTTTTCGCTCGTATCGTCATG

GGCACGGCATGTGATCTTTTCGGTCCACGTCTAGCCTCCGCCGCTTTGAC

GCTCTCCACCGCTCCCGCCGTCTATTTCACCGCCGGGATAAAGTCTCCGA

TCGGGTTTATCATGGTGAGATTCTTCGCCGGATTCTCTCTCGCCACTTTC

GTCTCGACTCAGTTCTGGATGAGCTCCATGTTCTCTGGACCCGTCGTGGG

TTCGGCTAACGGAATCGCCGCCGGGTGGGGTAACCTCGGAGGAGGCGCGA
```

CGCAGCTGATCATGCCCATCGTGTTCTCGTTGATTCGTAATATGGGAGCC

ACCAAGTTCACCGCGTGGAGGATCGCTTTTTTCATCCCCGGTCTCTTTCA

GACTCTCTCTGCTTTCGCCGTTCTCTTGTTCGGTCAGGTAACAAACCAAT

CACACTCACCGGTTCAGTTATTTTGGTTTTTTCAACTAATCCGGTTTTGA

GAATTTATCACCAAGTTATTTTTTGTTTTGGTTAAATTTACTTTCTTTGT

ATAGCCAGTTTATCCTGTTCTATATAAATGATTAAACCGATTCGTTTAGG

TGCAAACCCGGTTTATTGATACCGGTTTGGGTCGTCTAGTAGAGTCTTTA

GTCGGTTAATCATGGTCGAGTTTCAGTGGATATGGACAATAACTGTTTAA

TCATCTAAGTTGTGTCTATTACAAGGAATAGTAAAAGGATACATTTGTTT

TGTCTTATGTTTGCTATATGTTTTTGGAAATGAGTAGGATCTTCCTGATG

GAGATTATTGGGCGATGCATAAATCTGGAGAGAGGGAGAAAGATGATGTG

GGGAAAGTGATATCTAATGGAATCAAAAACTATAGGGGATGGATAACAGC

ATTAGCATATGGCTATTGTTTTGGAGTAGAGCTTACCATTGACAACATCA

TCGCAGAATATTTCTTCGATAGATTCCATTTAAAGCTCCAGACAGCAGGG

ATTATAGCAGCGAGTTTTGGACTAGCCAATTTTTTCGCTAGACCTGGAGG

AGGAATTTTCTCTGATTTTATGTCGAGACGGTTTGGGATGAGAGGAAGGT

TGTGGGCTTGGTGGATTGTGCAAACATCAGGAGGTGTATTATGCGCATGT

CTTGGCCAGATTTCTTCCTTGACAGTGTCTATAATTGTTATGCTTGTCTT

CTCTGTATTCGTCCAAGCCGCTTGTGGACTTACCTTTGGCGTTGTTCCCT

TTATTTCTAGAAGGTAACATACATTTTGGTATTGAGTTGCTTGATTGGTT

ATTCAACATTTTTGCTTACAAAAGTTTGTTTATGCAGATCTCTTGGGGTG

GTATCGGGAATGACTGGTGCGGGAGGCAATGTAGGCGCGGTCTTAACACA

GTTGATATTCTTCAAAGGATCGACATACACGAGAGAGACGGGTATAACTC

TAATGGGGGTAATGTCAATCGCATGTTCATTACCAATATGCTTGATTTAC

TTTCCGCAATGGGGAGGTATGTTTTGTGGACCCTCTTCCAAAAAAGCAAC

TGAAGAAGACTATTATCTCGCCGAATGGAACGATGAAGAGAAAGAAAAGA

ACTTACATATCGGAAGCCAAAAATTTGCGGAAACCAGCATTAGCGAAAGA

GGTCGAGCCACAACGACTCATCCCCAAACTTGA
```

The cDNA sequence (exons only) encoding one embodiment of *Arabidopsis* nitrate transporter Nrt2.5 is provided herein as SEQ ID No. 2, as follows:

```
                                           [SEQ ID No. 2]
ATGGAGGTCGAAGGCAAAGGAGGAGAAGCTGGAACCACCACCACAACCGC

ACCTCGGAGGTTCGCACTTCCGGTGGACGCGGAGAACAAAGCAACAACTT

TCCGACTATTCTCAGTCGCTAAACCTCACATGAGAGCTTTCCATCTCTCA

TGGTTTCAATTCTTTTGCTGCTTCGTCTCCACTTTCGCAGCTCCGCCTCT

CCTCCCTGTTATCCGTGAAAATCTTAACCTCACCGCCACCGACATCGGAA

ACGCCGGAATAGGGTCTGTCTCCGGCGCTGTTTTCGCTCGTATCGTCATG

GGCACGGCATGTGATCTTTTCGGTCCACGTCTAGCCTCCGCCGCTTTGAC

GCTCTCCACCGCTCCCGCCGTCTATTTCACCGCCGGGATAAAGTCTCCGA

TCGGGTTTATCATGGTGAGATTCTTCGCCGGATTCTCTCTCGCCACTTTC
```

```
                                                    -continued
GTCTCGACTCAGTTCTGGATGAGCTCCATGTTCTCTGGACCCGTCGTGGG

TTCGGCTAACGGAATCGCCGCCGGGTGGGGTAACCTCGGAGGAGGCGCGA

CGCAGCTGATCATGCCCATCGTGTTCTCGTTGATTCGTAATATGGGAGCC

ACCAAGTTCACCGCGTGGAGGATCGCTTTTTTCATCCCCGGTCTCTTTCA

GACTCTCTCTGCTTTCGCCGTTCTCTTGTTCGGTCAGGATCTTCCTGATG

GAGATTATTGGGCGATGCATAAATCTGGAGAGAGGGAGAAAGATGATGTG

GGGAAAGTGATATCTAATGGAATCAAAAACTATAGGGGATGGATAACAGC

ATTAGCATATGGCTATTGTTTTGGAGTAGAGCTTACCATTGACAACATCA

TCGCAGAATATTTCTTCGATAGATTCCATTTAAAGCTCCAGACAGCAGGG

ATTATAGCAGCGAGTTTTGGACTAGCCAATTTTTTCGCTAGACCTGGAGG

AGGAATTTTCTCTGATTTTATGTCGAGACGGTTTGGGATGAGAGGAAGGT

TGTGGGCTTGGTGGATTGTGCAAACATCAGGAGGTGTATTATGCGCATGT

CTTGGCCAGATTTCTTCCTTGACAGTGTCTATAATTGTTATGCTTGTCTT

CTCTGTATTCGTCCAAGCCGCTTGTGGACTTACCTTTGGCGTTGTTCCCT

TTATTTCTAGAAGATCTCTTGGGGTGGTATCGGGAATGACTGGTGCGGGA

GGCAATGTAGGCGCGGTCTTAACACAGTTGATATTCTTCAAAGGATCGAC

ATACACGAGAGACGGGTATAACTCTAATGGGGGTAATGTCAATCGCAT

GTTCATTACCAATATGCTTGATTTACTTTCCGCAATGGGGAGGTATGTTT

TGTGGACCCTCTTCCAAAAAAGTAACTGAAGAAGACTATTATCTCGCCGA

ATGGAACGATGAAGAGAAAGAAAAGAACTTACATATCGGAAGCCAAAAAT

TTGCGGAAACCAGCATTAGCGAAAGAGGTCGAGCCACAACGACTCATCCC

CAAAGTTGA
```

Accordingly, the coding sequence, which encodes the polypeptide having nitrate transporter activity, may comprise a nucleic acid sequence substantially as set out in either SEQ ID No. 1 or SEQ ID No. 2, or a functional variant or fragment or orthologue thereof.

The polypeptide sequence of the *Arabidopsis* NRT2.5 nitrate transporter is provided herein as SEQ ID No. 3, follows:

```
                                                        [SEQ ID No. 3]
MEVEGKGGEAGTTTTTAPRRFALPVDAENKATTFRLFSVAKPHMRAFHLS

WFQFFCCFVSTFAAPPLLPVIRENLNLTATDIGNAGIASVSGAVFARIVM

GTACDLFGPRLASAALTLSTAPAVYFTAGIKSPIGFIMVRFFAGFSLATF

VSTQFWMSSMFSGPVVGSANGIAAGWGNLGGGATQLIMPIVFSLIRNMGA

TKFTAWRIAFFIPGLFQTLSAFAVLLFGQDLPDGDYWAMHKSGEREKDDV

GKVISNGIKNYRGWITALAYGYCFGVELTIDNIIAEYFFDRFHLKLQTAG

IIAASFGLANFFARPGGGIFSDFMSRRFGMRGRLWAWWIVQTSGGVLCAC

LGQISSLTVSIIVMLVFSVFVQAACGLTFGVVPFISRRSLGVVSGMTGAG

GNVGAVLTQLIFFKGSTYTRETGITLMGVMSIACSLPICLIYFPQWGGMF

CGPSSKKVTEEDYYLAEWNDEEKEKNLHIGSQKFAETSISERGRATTTHP

QT
```

In order to obtain an indication of how over-expression of the constructs of the invention effected nitrogen distribution within the transgenic plants, the inventors measured the amino acid content of the transgenic and wild-type plants, as shown in FIGS. 3 and 4. They were surprised to observe that over-expression of the nitrate transporter via the genetic construct resulted in a considerable decrease in the amino acid content of the upper leaves. Furthermore, as shown in FIG. 5, over-expression of the nitrate transporter also caused a significant decrease in the nitrate concentration in both the top and the bottom leaves. Based on these results, the inventors also expect the TSNA content of the upper leaves to be reduced.

The promoter may be capable of inducing RNA polymerase to bind to, and start transcribing, the coding sequence encoding the polypeptide having nitrate transporter activity. The promoter in constructs of the invention may be a constitutive, non-constitutive, tissue-specific, developmentally-regulated or inducible/repressible promoter.

A constitutive promoter directs the expression of a gene throughout the various parts of the plant continuously during plant development, although the gene may not be expressed at the same level in all cell types. Examples of known constitutive promoters include those associated with the rice actin 1 gene (Zhang et al., 1991, Plant Cell, 3, 1155-65) and the maize ubiquitin 1 gene (Cornejo et al., 1993, Plant Molec. Biol., 23, 567-581). Constitutive promoters such as the Carnation Etched Ring Virus (CERV) promoter (Hull et al., 1986, EMBO J., 5, 3083-3090) are particularly preferred in the present invention.

A tissue-specific promoter is one which directs the expression of a gene in one (or a few) parts of a plant, usually throughout the life-time of those plant parts. The category of tissue-specific promoter commonly also includes promoters whose specificity is not absolute, i.e. they may also direct expression at a lower level in tissues other than the preferred tissue. Examples of tissue-specific promoters known in the art include those associated with the patatin gene expressed in potato tuber, and the high molecular weight glutenin gene expressed in wheat, barley or maize endosperm.

A developmentally-regulated promoter directs a change in the expression of a gene in one or more parts of a plant at a specific time during plant development, e.g. during senescence. The gene may be expressed in that plant part at other times at a different (usually lower) level, and may also be expressed in other plant parts.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter can be described as a specific type of inducible promoter responding to an endogenous inducer produced by the plant or to an environmental stimulus at a particular point in the life cycle of the plant. Examples of known inducible promoters include those associated with wound response, temperature response, and chemically induced.

The promoter may be obtained from different sources including animals, plants, fungi, bacteria, and viruses, and different promoters may work with different efficiencies in different tissues. Promoters may also be constructed synthetically. Therefore, examples of suitable promoters include the Carnation Etched Ring Virus (CERV) promoter, the pea plastocyanin promoter, the rubisco promoter, the nopaline synthase promoter, the chlorophyll a/b binding promoter, the high molecular weight glutenin promoter, the α,β-gliadin promoter, the hordein promoter, the patatin promoter, or a senescence-specific promoter. For example, a suitable senescence-specific promoter may be one which is derived from a senescence-associated gene (SAG), and may be selected from a group consisting of SAG12, SAG13, SAG101, SAG21 and SAG18.

Preferably, the promoter is the CERV promoter, as shown in the construct illustrated in FIG. 2.

Thus, according to a second aspect of the invention, there is provided a genetic construct comprising a Carnation Etched Ring Virus (CERV) promoter operably linked to a coding sequence encoding a polypeptide having nitrate transporter activity, wherein the polypeptide comprises an amino acid sequence as set out in SEQ ID No.3, or a functional variant or fragment or orthologue thereof.

The promoter may be a Carnation Etched Ring Virus (CERV) promoter, which will be known to the skilled technician, or a functional variant or a fragment thereof (Hull et al., EMBO J., 5, 3083-3090). The DNA sequence encoding the CERV promoter is 232 bp long, and is referred to herein as SEQ ID No-4, as follows:

[SEQ ID No. 4]
AGCTTGCATGCCTGCAGGTCGAGCTTTTAGGATTCCATAGTGATAAGATA

TGTTCTTATCTAAACAAAAAAGCAGCGTCGGCAAACCATACAGCTGTCCA

CAAAAAGGAAAGGCTGTAATAACAAGCGGACCCAGCTTCTCAGTGGAAGA

TACTTTATCAGACACTGAATAATGGATGGACCCTACCACGATTAAAGAGG

AGCGTCTGTCTAAAGTAAAGTAGAGCGTCTTT

Therefore, the promoter in the construct of the invention may comprise a nucleotide sequence substantially as set out in SEQ ID No. 4, or a functional variant or functional fragment thereof. The CERV promoter may be obtained from Cauliovirus or a plant species such as *Dianthus caryophyllus* (i.e. carnation) showing signs of the cauliovirus. In embodiments where the promoter is the CERV promoter, it will be appreciated that the promoter may comprise each of the bases 1-232 of SEQ ID No. 4. However, functional variants or functional fragments of the promoter may also be used in genetic constructs of the invention.

A "functional variant or functional fragment of a promoter" can be a derivative or a portion of the promoter that is functionally sufficient to initiate expression of any coding region that is operably linked thereto. For example, in embodiments where the promoter is based on the CERV promoter, the skilled technician will appreciate that SEQ ID No. 4 may be modified, or that only portions of the CERV promoter may be required, such that it would still initiate gene expression in the construct.

Functional variants and functional fragments of the promoter may be readily identified by assessing whether or not transcriptase will bind to a putative promoter region, and then lead to the transcription of the coding region into the polypeptide having nitrate transporter activity. Alternatively, such functional variants and fragments may be examined by conducting mutagenesis on the promoter, when associated with a coding region, and assessing whether or not gene expression may occur.

The polypeptide having nitrate transporter activity in the construct of the first or second aspect may be derived from any suitable source, such as a plant. The coding sequence, which encodes the polypeptide having nitrate transporter activity, may be derived from a suitable plant source, for example from *Arabidopsis* spp., *Oryza* spp., *Populus* spp. or *Nicotiana* spp. The coding sequence may be derived from *Arabidopsis thaliana, Oryza sativa, Populus tremula* or *Nicotiana tabacum*. It will be appreciated that orthologues are genes or proteins in different species that evolved from a common ancestral gene by speciation, and which retain the same function.

The inventors have created a construct in which the CERV promoter has been used to drive expression of the nitrate transporter protein (NRT2.5) from *Arabidopsis thaliana*.

The construct may be capable of decreasing, in a plant transformed with a construct of the invention, the concentration of nitrate by at least 5%, 10%, 15%, 18%, 20%, 32%, 35%, 38%, 40%, 50%, 60% or 63% compared to the concentration of nitrate in the wild-type plant (i.e. which has not been transformed with a construct of the invention), preferably grown under the same conditions.

The construct may be capable of decreasing, in a plant transformed with the construct, the concentration of 4-(Methylnitrosamino)-1-(3-pyridyl)-1-butanone (NNK) by at least 10%, 20%, 30%, 40%, 50%, 60%, 61%, 62%, 65%, 69%, 71% or 75%, compared to the concentration of NNK in the wild-type plant, preferably grown under the same conditions.

The construct may be capable of decreasing, in a plant transformed with the construct, the concentration of N-Nitrosonornicotine (NNN) by at least 10%, 20%, 30%, 40%, 50%, 60%, 70%, 71%, 75%, 78%, 80%, 82%, 84%, 85%, 88%, 90% or 94%, compared to the concentration of NNN in the wild-type plant, preferably grown under the same conditions.

The construct may be capable of decreasing, in a plant transformed with the construct, the concentration of N-Nitrosoanatabine (NAT) by at least 5%, 6%, 10%, 20%, 23%, 24%, 30%, 40%, 46%, 45%, 48%, 50%, 60%, 70%, 80% or 85%, compared to the concentration of NAT in the wild-type plant, preferably grown under the same conditions.

The construct may be capable of decreasing, in a plant transformed with the construct, the concentration of total tobacco-specific nitrosamines (TSNA) by at least 10%, 20%, 30%, 40%, 50%, 56%, 60%, 64%, 65%, 70% or 75% compared to the concentration of total TSNA in the wild-type plant, preferably grown under the same conditions. Preferably, the construct is capable of decreasing the concentration of any of the compounds selected a group of compounds including nitrate, NNK, NNN, NAT and total TSNA, in a leaf or stem from a plant of a T0, T1 and/or T2 plant population. The inventors have shown in the Examples that over-expression of AtNrt2.5 results in increased remobilisation of nitrate in the leaf in the test or transgenic plant compared to that of the wild-type. This nitrate remobilisation is believed to be mediated through remobilisation of amino acids such as Gln, Asn and Pro, out of the leaf. This is demonstrated by lower levels of these amino acids in both source tissues (i.e. lower leaves) and sink leaves (i.e. top leaves) (see the Figures). The construct may therefore be capable of decreasing Gln, Asn and/or Pro concentrations in the leaf.

The construct may be capable of decreasing the concentrations of any of these compounds (i.e. nitrate, amino acids involved in nitrogen assimilation, total TSNA, NNN, NAT or NNK) in a leaf located at a lower, middle or upper position on the plant. "Lower position" can mean in the lower third of the plant (for example leaf number 4 or 5 from the base of the plant), "upper position" can mean in the upper third of the plant (for example leaf number 14 or 15 from the base of the plant), and "middle position" can mean the central third of the plant between the lower and upper positions (for example leaf number 10 or 11 from the base of the plant). At the time of sampling, the total number of leaves is approximately 20.

Genetic constructs of the invention may be in the form of an expression cassette, which may be suitable for expression of the coding sequence encoding a nitrate transporter in a host cell. The genetic construct of the invention may be introduced in to a host cell without it being incorporated in a vector. For instance, the genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly into cells of a host subject (e.g. a plant) by transfection, infection, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Hence, in a third aspect, there is provided a recombinant vector comprising the genetic construct according to the first or second aspect.

The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19 (Bevan M., 1984, Nucleic Acids Research 12:8711-21).

Recombinant vectors may include a variety of other functional elements in addition to the promoter (e.g. a CERV), and the coding sequence encoding a nitrate transporter. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector of the third aspect may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sul respectively; EP-A-242246, EP-A-0249637); and screenable markers such as beta-glucuronidase (GB2197653), luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

The various embodiments of genetic constructs of the invention may be prepared using the cloning procedure described in the Examples, which may be summarised as follows. The genomic or cDNA versions of the genes encoding the nitrate transporter may be amplified from the genomic or cDNA templates by PCR using suitable primers, for example SEQ ID No's 5 and 6. PCR products may then be examined using agarose gel electrophoresis. The PCR products may then be ligated into a suitable vector for cloning purposes, for example that which is sold under the trade name pCR4-TOPO (available from Invitrogen). Vectors harbouring the PCR products may be grown up in a suitable host, such as *E. coli*. *E. coli* colonies may then be screened by PCR using suitable primers, and inserts in plasmids showing the correct restriction enzyme digest pattern may be sequenced using suitable primers.

*E. coli* colonies carrying pCR4-TOPO-genomic DNA (Atnrt2.5) may be cultured to produce a suitable amount of each plasmid, which may then be purified. The plasmids may then be digested to release a DNA fragment encoding the Atnrt2.5, which may then be cloned into a vector harbouring a suitable promoter, for example either the CERV promoter, such as a pBNP plasmid (van Engelen et al., 1995, Transgenic Research, 4:288-290).

The resultant Atnrt2.5 construct, contained the CERV promoter and was named CRVAtNRT2.5. Embodiments of the vector according to the third aspect may be substantially as set out in FIG. 2.

In view of their surprising results, the inventors believe that they are the first to have developed a method for decreasing nitrate concentrations in plant leaves using the expression of an exogenous nitrate transporter gene (e.g. AtNRT2.5) in a transgenic plant.

Hence, in a fourth aspect, there is provided a method of decreasing the nitrate concentration in the leaves of a test plant to below that of the corresponding nitrate concentration in leaves of a wild-type plant cultured under the same conditions, the method comprising:—
(i) transforming a plant cell with the genetic construct according to the first or second aspect, or the vector according to the third aspect; and
(ii) regenerating a plant from the transformed cell.

In a fifth aspect of the invention, there is provided a method of producing a transgenic plant which transports nitrate out of a leaf at a higher rate than a corresponding wild-type plant cultured under the same conditions, the method comprising:—
(i) transforming a plant cell with the genetic construct according to the first or second aspect, or the vector according to the third aspect; and
(ii) regenerating a plant from the transformed cell.

In a sixth aspect, there is provided a method for producing a transgenic plant, the method comprising introducing, into an unmodified plant, an exogenous gene encoding a nitrate transporter polypeptide, wherein the polypeptide comprises an amino acid sequence as set out in SEQ ID No. 3, or a functional variant or fragment or an orthologue thereof, and wherein expression of the nitrate transporter encoded by the exogenous gene reduces the nitrate concentration in the leaves of the transgenic plant relative to the concentration of nitrate in the leaves of the unmodified plant.

The position of a leaf in relation to the rest of the plant (i.e. whether it is regarded as being within the "lower" position, the "top" position or the "middle" position) is important for tobacco growers. The physiology, and therefore, the quality and the flavour of a leaf are strongly related to its position within a plant. As a plant approaches flowering, a process called remobilization occurs, and it involves the transport of nutrients, such as amino acids and nitrogenous compounds, from the base of the plant towards the top of the plant. Remobilized nutrients will be used as an energy source for seed production. Consequently, the lower leaves will have a different nitrogen content compared to the upper leaves of the plant, which is illustrated by a different amino acid profile, as shown in FIGS. 3 and 4. Lower leaves are called "source leaves" and the top leaves are called "sink leaves". The middle leaves are fully expanded mature green leaves.

With respect to some plants, such as tobacco, by removing the flower head of the plant, changes in leaf nutrient metabolism can be generated. These changes allow the remobilized nutrients to be used in the leaves, and result in thickened leaves, general growth of the leaves and the production of nitrogen-rich secondary metabolites, many of which are the precursors of the flavours that are later found in cured leaves. Therefore, constructs of the invention may be used to modify the flavour of a transgenic plant.

As shown in FIG. 7, the inventors were surprised to observe that the genetic constructs according to the invention may also be capable of modulating (i.e. increasing and/or decreasing) the concentration of certain amino acids that are known to involved in nitrate metabolism (e.g. Gln, Asn, Asp, Glu and/or Pro), in the leaves of a transgenic plant, which are found in the upper, middle or lower position, compared to corresponding leaves that are found in a wild-type plant grown under the same conditions.

Accordingly, in a seventh aspect, there is provided a method of modulating the profile of amino acids involved in the nitrogen assimilation of leaves of a test plant compared to the amino acid profile of corresponding leaves of a wild-type plant cultured under the same conditions, the method comprising:—
(i) transforming a plant cell with the genetic construct according to the first or second aspect, or the vector according to the third aspect; and
(ii) regenerating a plant from the transformed cell.

In an eighth aspect, there is provided a method of modulating the profile of amino acids involved in the nitrogen assimilation pathway of a harvested leaf taken from a transgenic plant, compared to the amino acid profile of a corresponding harvested leaf taken from a wild-type plant cultured under the same conditions, wherein the leaf is harvested from a transgenic plant produced by the method according to either the fifth or sixth aspect.

According to the invention, amino acids involved in the nitrogen assimilation pathway of plants and their leaves may comprise glutamine (Gln), asparagine (Asn), aspartic acid (Asp), glutamic acid (Glu) or proline (Pro), and so any of the profile or any or all of these amino acids may be modulated.

The construct may be capable of decreasing or increasing, in a plant transformed with the construct, the concentration of at least one amino acid involved in the nitrogen assimilation pathway by at least 10%, 20%, 30%, 40%, 50%, 56%, 60%, 64%, 65%, 70% or 75% compared to the concentration of the at least one amino acid in a wild-type plant grown under the same conditions.

Preferably, the construct results in the decrease in concentration of the amino acid. Preferably, the construct may be capable of decreasing the concentration of the amino acids Pro and Gln in the leaves (preferably the lower leaves) of a transgenic plant compared to corresponding leaves that are found in a wild-type plant grown under the same conditions. The construct may also be capable of reducing the concentration of the amino acids Gln, Asn, Asp, Glu and/or Pro in leaves, which are found in the upper position of a transgenic plant compared to corresponding leaves that are found in a wild-type plant grown under the same conditions.

In a ninth aspect, there is provided a transgenic plant comprising the genetic construct according to the first or second aspect, or the vector according to the third aspect.

In an tenth aspect, there is provided a transgenic plant comprising an exogenous gene encoding a nitrate transporter polypeptide, wherein the polypeptide comprises an amino acid sequence as set out in SEQ ID No. 3, or a functional variant or fragment or an orthologue thereof, and wherein the nitrate concentration in the leaves of the transgenic plant is reduced compared to the nitrate concentration in the leaves of an unmodified plant.

In a eleventh aspect, there is provided use of an exogenous nucleic acid sequence encoding a nitrate transporter polypeptide for reducing nitrate concentration in plant leaves by transformation of the plant with the exogenous nucleic acid sequence, the polypeptide comprising an amino acid sequence as set out in SEQ ID No. 3, or a functional variant or fragment or an orthologue thereof.

The term "unmodified plant" can mean a plant before transformation with an exogenous gene or a construct of the invention. The unmodified plant may therefore be a wild-type plant.

The term "exogenous gene" can mean the gene that is transformed into the unmodified plant is from an external source, i.e. from a different species to the one being transformed. The exogenous gene may have a nucleic acid sequence substantially the same or different to an endogenous gene encoding a nitrate transporter in the unmodified plant. The exogenous gene may be derived from a genomic or cDNA sequence encoding the *Arabidopsis thaliana* nrt2.5 gene or an orthologue thereof. The exogenous gene may form a chimeric gene, which may itself constitute a genetic construct according to the first or second aspect. The exogenous gene may encode a nitrate transporter having the amino acid sequence substantially as set out in SEQ ID No. 3, or a functional variant or fragment or orthologue thereof. The exogenous gene may comprise the nucleotide sequence substantially as set out in either SEQ ID No. 1 or SEQ ID No. 2, or a functional variant or fragment or orthologue thereof.

Methods for determining the level of nitrate in plant leaves are set out in the Examples. The methods and uses of the invention may comprise transforming a test plant cell or unmodified plant cell with a genetic construct according to the first or second aspect, a vector according to the third aspect, or the exogenous gene described herein.

Thus, in an twelfth aspect, there is provided a host cell comprising the genetic construct according to the first or second aspect, or the recombinant vector according to the third aspect.

The cell may be a plant cell. The cell may be transformed with a genetic construct, vector or exogenous gene according to the invention, using known techniques. Suitable means for introducing the genetic construct into the host cell may include use of a disarmed Ti-plasmid vector carried by *Agrobacterium* by procedures known in the art, for example as described in EP-A-0116718 and EP-A-0270822. A further method may be to transform a plant protoplast, which involves first removing the cell wall and introducing the nucleic acid, and then reforming the cell wall. The transformed cell may then be grown into a plant.

Preferably, and advantageously, the methods and uses according to the invention do not compromise the health or fitness of the test or transgenic plant that is generated. The inventors have observed that over-expressing the Atnrt2.5 nitrate transporter in a plant host cell is effective at inducing nitrate transport from the plant's leaves. Hence, it is preferred that the methods and uses of the invention comprise transforming the test plant with the construct of the invention such that the nitrate transporter is over-expressed.

The transgenic or test plants according to invention may include the Brassicaceae family, such as *Brassica* spp. The plant may be *Brassica napus* (oilseed rape). Further examples of transgenic or test plants include the family Poales, such as Triticeae spp. The plant may be *Triticum* spp. (wheat). Increasing the grain protein content in wheat may result in increased volume of food products comprising wheat, such as bread.

Further examples of suitable transgenic or test plants according to the invention may include the Solanaceae family of plants which include, for example jimson weed, eggplant, mandrake, deadly nightshade (*belladonna*), *capsicum* (paprika, chilli pepper), potato and tobacco. One example of a suitable genus of Solanaceae is *Nicotiana*. A suitable species of *Nicotiana* may be referred to as tobacco plant, or simply tobacco.

Further examples of suitable transgenic or test plants according to the invention may include leafy crops such as the Asteraceae family of plants which, for example, include lettuce (*Lactuca sativa*). Another example may include the Chenopodiaceae family of plants, which includes *Spinacia oleracea* and *Beta vulgaris*, i.e. spinach and chards, respectively.

Tobacco may be transformed with constructs, vectors and exogenous genes of the invention as follows.

*Nicotiana tabacum* is transformed using the method of leaf disk co-cultivation essentially as described by Horsch et al. (Science 227: 1229-1231, 1985). The youngest two expanded leaves were be taken from 7-week old tobacco plants and were surface-sterilised in 8% Domestos™ for 10 minutes and washed (3 rinses) times with sterile distilled water. Leaf disks were then cut using a number 6 cork borer and placed in the *Agrobacterium* suspension, containing the appropriate binary vectors (as described in the Examples), for approximately two minutes. The discs were then gently blotted between two sheets of sterile filter paper. Ten disks may be placed on MS 3% sucrose+2.2 µM BAP+0.27 µM NAA plates, which were then incubated for 2 days in the growth room. The discs may be transferred to plates of MS media+3% sucrose+2.2 µM BAP+0.27 µM NAA supplemented with 500 g/l Cefotaxime and 100 mg/l kanamycin. After 2 weeks, the discs were transferred onto fresh plates of above medium. After a further two weeks, the leaf disks were transferred onto plates containing LS media+3% sucrose+0.5 µM BAP supplemented with 500 mg/l Cefotaxime and 100 mg/l kanamycin. The leaf disks were then transferred onto fresh medium every two weeks. Shoots were excised as they appeared and transferred to jars of LS media+3% sucrose+0.5 µM BAP supplemented with 500 mg/l claforan. The shoots in jars were then transferred, in jars, to LS media+3% sucrose+250 mg/l Cefotaxime after approximately 3 weeks. After a further 3-4 weeks the plants were then transferred to IS media+3% sucrose (without antibiotics) and rooted. Once the plants were rooted they were transferred to soil in the greenhouse.

In a thirteenth aspect, there is provided a plant propagation product obtainable from the transgenic plant according to either the ninth or tenth aspect.

A "plant propagation product" may be any plant matter taken from a plant from which further plants may be produced. Suitably, the plant propagation product may be a seed. The plant propagation product may preferably comprise a construct or vector according to the invention or an exogenous gene.

The inventors have observed that a leaf of a test plant (i.e. a transgenic plant) which has been transformed with a construct according to the invention exhibits increases in nitrate remobilisation out of the leaf such that the concentration of nitrate, which is a precursor to TSNAs such as NNK, NNN and/or NAT, decreases in the leaf. Clearly, such a leaf therefore would be particularly advantageous.

Therefore, in a fourteenth aspect of the invention, there is provided a harvested leaf containing a lower level of nitrate than the corresponding level of nitrate in a harvested leaf taken from a wild-type plant cultured under the same conditions, wherein the leaf is harvested from the transgenic plant according to either the ninth or tenth aspect, or produced by the method according to either the fifth or sixth aspect.

In a fifteenth aspect of the invention, there is provided a tobacco product comprising nitrate-reduced tobacco obtained from a mutant tobacco plant comprising the construct of the first or second aspect or the vector of the third aspect, which mutant is capable of decreasing the concentration of nitrate in its leaves.

It is preferred that the mutant tobacco plant from which the tobacco in the tobacco product is derived comprises a construct, vector or exogenous gene according to the invention.

The tobacco product may be smokeless tobacco product, such as snuff. The tobacco product may be an oral tobacco product deliverable by the mouth. The tobacco product may be moist, and may be snus. However, the tobacco product may also be a smoking article.

Thus, in a sixteenth aspect, there is provided a smoking article comprising nitrate-reduced tobacco obtained from a mutant tobacco plant comprising the construct of the first or second aspect or the vector of the third aspect, which mutant is capable of decreasing the concentration of nitrate in its leaves.

Nitrate-reduced tobacco can include tobacco in which the nitrate concentration is less than the corresponding concentration in a wild-type plant cultured under the same conditions. Such a smoking article may comprise tobacco obtained from a mutant tobacco plant, which may have been transformed with a genetic construct according to the first or second aspect of the invention, or a vector according to the third aspect, or an exogenous gene. Preferably, the mutant tobacco plant comprises the nitrate transporter, AtNRT2.5.

The term "smoking article" can include smokable products, such as rolling tobacco, cigarettes, cigars and cigarillos whether based on tobacco, tobacco derivatives, expanded tobacco, reconstituted tobacco or tobacco substitutes and also heat-not-burn products.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the gene identified as SEQ ID No. 1 or 2 (which encodes one embodiment of a nitrate transporter), or 40% identity with the polypeptide identified as SEQ ID No. 3 (i.e. one embodiment of a nitrate transporter).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:— Sequence Identity=(N/T)*100.

Alternative methods for identifying similar sequences will be known to those skilled in the art. For example, a substantially similar nucleotide sequence will be encoded by a sequence which hybridizes to the sequences shown in either SEQ ID No. 1 or SEQ ID No. 2, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No. 3.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

In order to address various issues and advance the art, the entirety of this disclosure shows by way of illustration various embodiments in which the claimed invention(s) may be practiced and provide for superior method for reducing the nitrate concentration in the leaves of transgenic plants. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 5A:
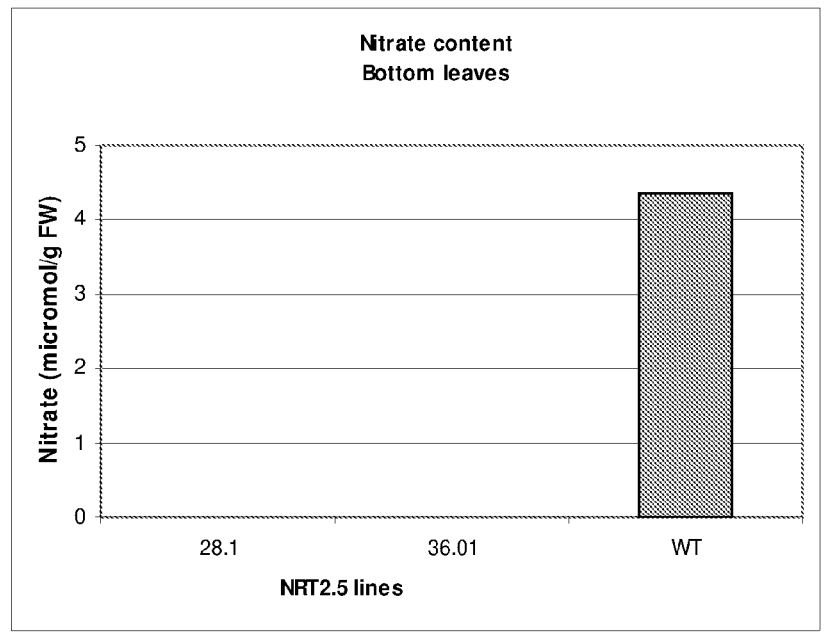
Figure 5B:
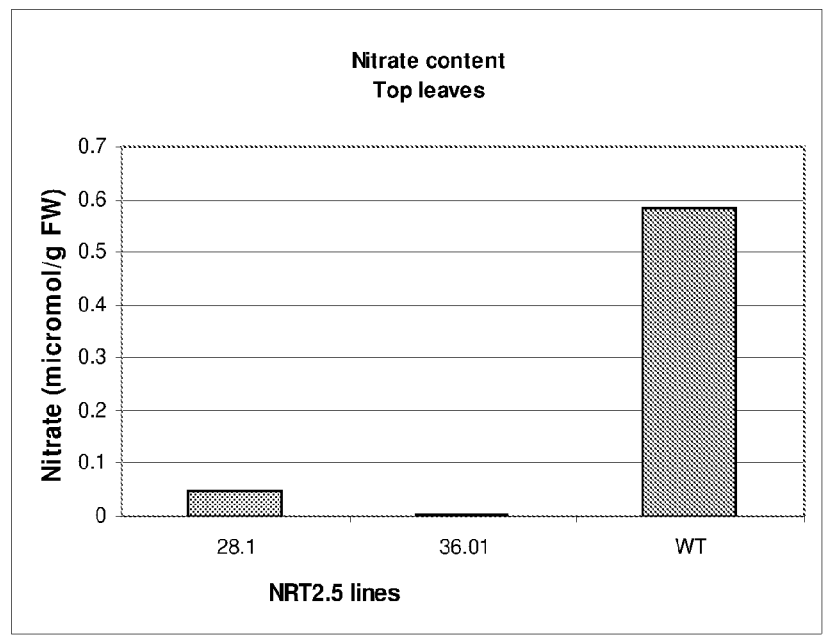
Figure 6:
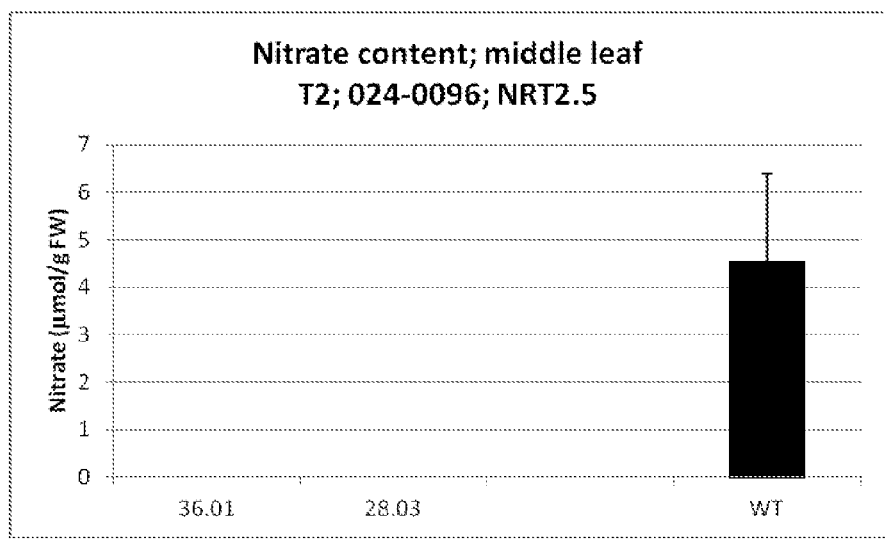
Figure 7:
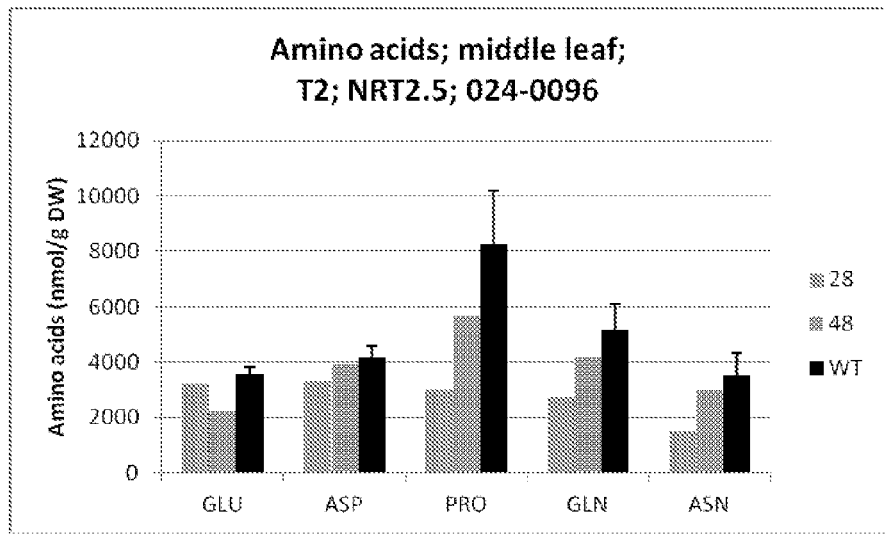

FIG. 3A-E shows the concentration of various amino acids (i.e. Glutamine (Gln), Asparagine (Asn), Aspartic Acid (Asp), Glutamic Acid (Glu) and Proline (Pro) respectively) in the top leaves of two Burley PH2517 plant lines (i.e. 28.1 and 36.01) harbouring the promoter CERV::NRT2.5 construct (Wild-type [WT] Burley PH2517 acted as control);

FIG. 4A-E shows the concentration of various amino acids (i.e. Glutamine (Gln), Asparagine (Asn), Aspartic Acid (Asp), Glutamic Acid (Glu) and Proline (Pro) respectively) in the bottom leaves of two Burley PH2517 plant lines (i.e. 28.1 and 36.01) harbouring the promoter CERV::NRT2.5 construct (Wild-type [WT] Burley PH2517 acted as control); and FIG. 5A shows the concentration of nitrate in the bottom leaves of two Burley PH2517 plant lines (i.e. 28.1 and 36.01) harbouring the promoter CERV::NRT2.5 construct (Wild-type [WT] Burley PH2517 acted as control), FIG. 5B shows the concentration of nitrate in the top leaves of two Burley PH2517 plant lines (i.e. 28.1 and 36.01) harbouring the promoter CERV::NRT2.5 construct (Wild-type [WT] Burley PH2517 acted as control);

FIG. 6 shows the concentration of nitrate in the middle leaves of two T2 lines (i.e. 36.01 and 28.03) harbouring the promoter CERV::NRT2.5 construct (Wild type [WT] Burley PH2517 acted as control); and FIG. 7 shows the amino acid profile in the middle leaf of two T2 lines (i.e. 28 and 48) harbouring the promoter CERV::NRT2.5 construct (Wild type [WT] Burley PH2517 acted as control).

DETAILED DESCRIPTION & EXAMPLES

Figure 1:
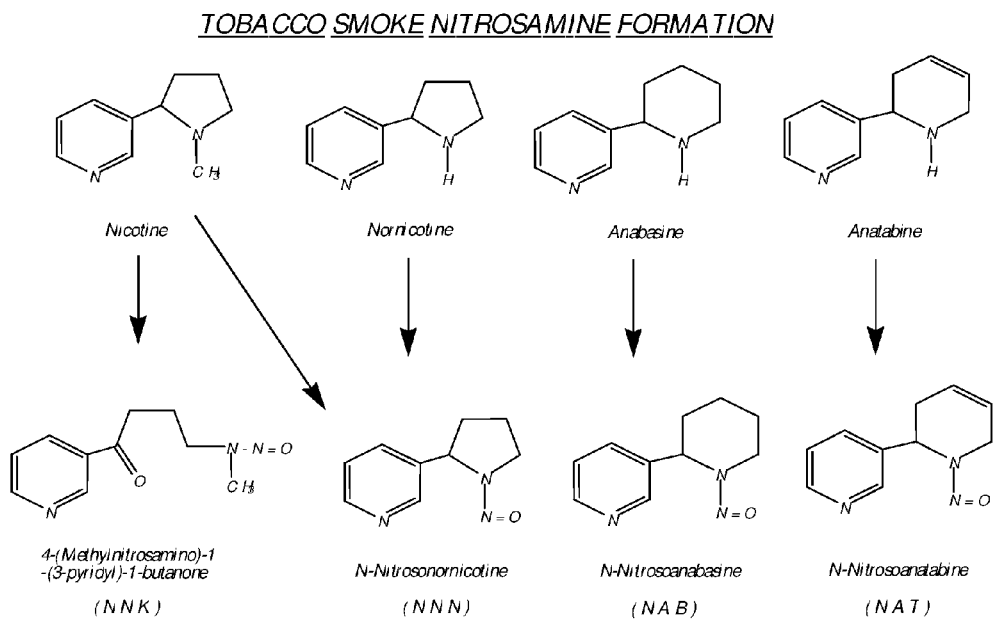
FIG. 1 shows the chemical structures of various tobacco smoke nitrosamines, 4-(Methylnitrosamino)-1-(3-pyridyl)-1-butanone (NNK), N-Nitrosonornicotine (NNN), N-Nitrosoanabasine (NAB) and N-Nitrosoanatabine (NAT)
Figure 2:
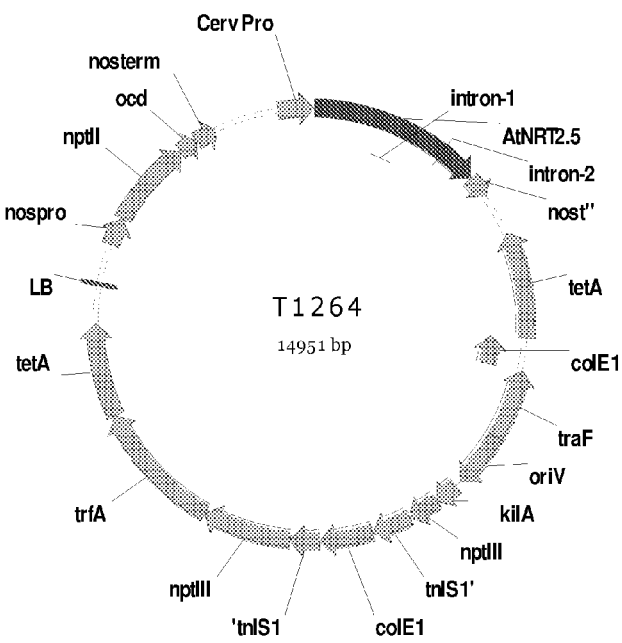
FIG. 2 is a plasmid map of one embodiment of a construct according to the invention, known as pGNP024 0096 001. The construct includes the Atnrt2.5 nitrate transporter gene under the control of the Carnation Etched Ring Virus (CERV) promoter.
Figure 3A:
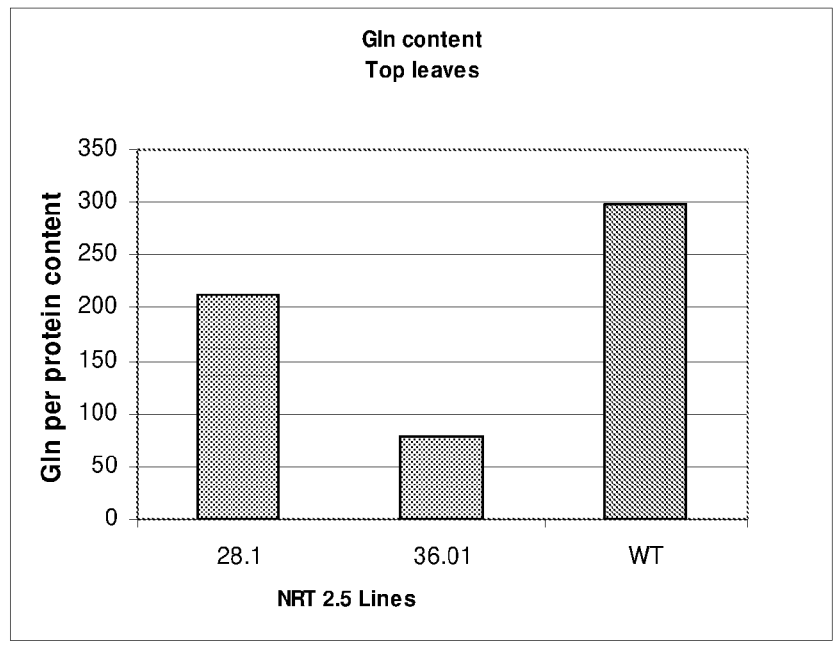
Figure 3B:
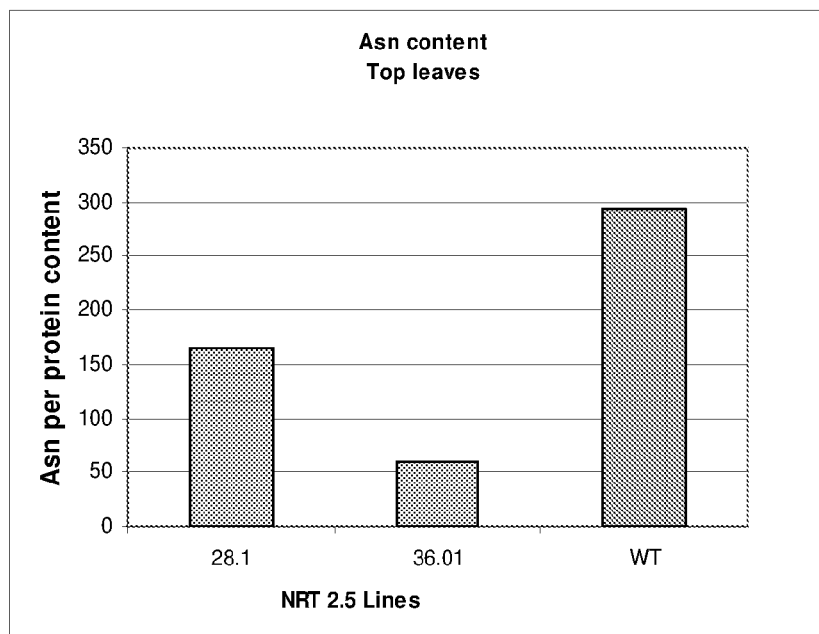
Figure 3C:
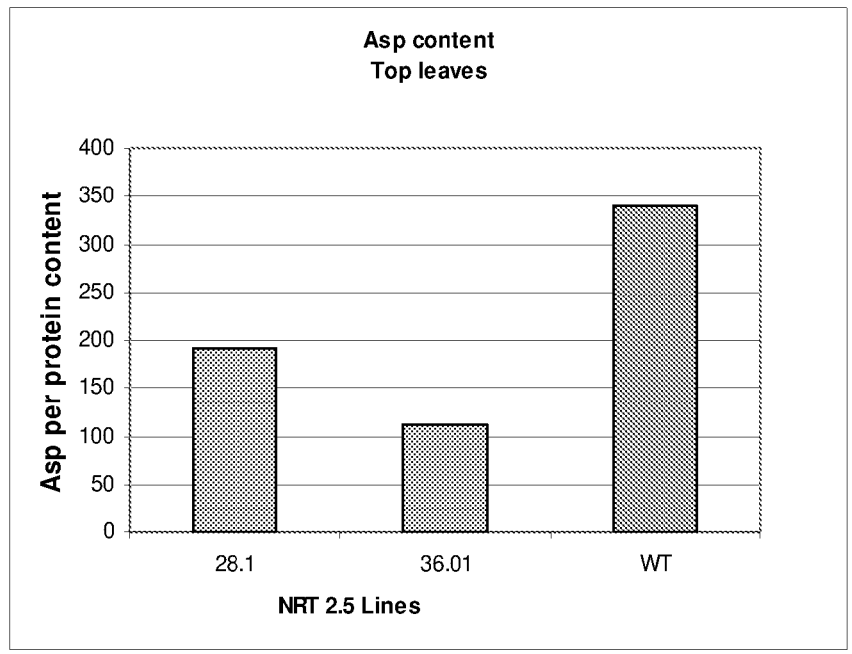
Figure 3D:
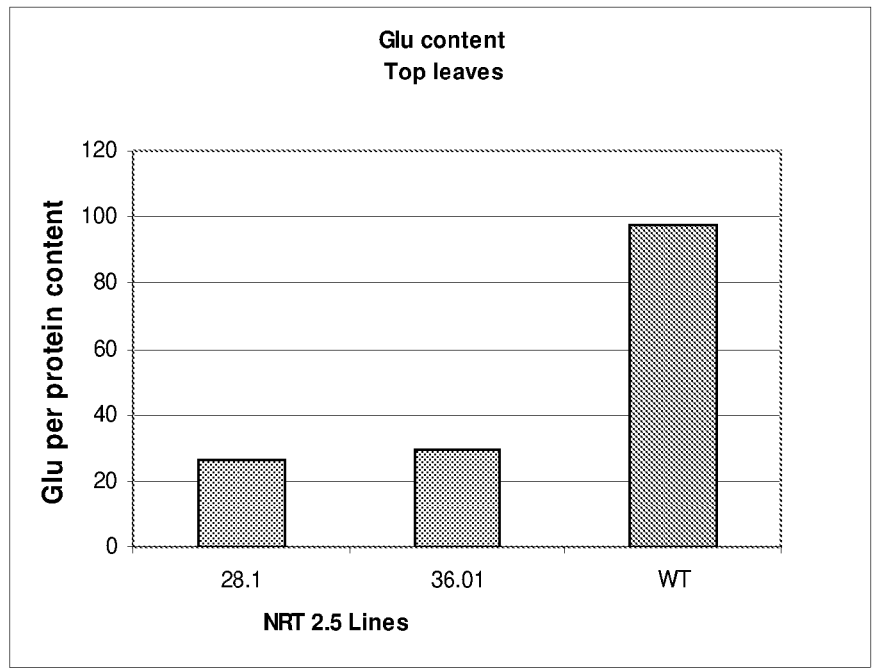
Figure 3E:
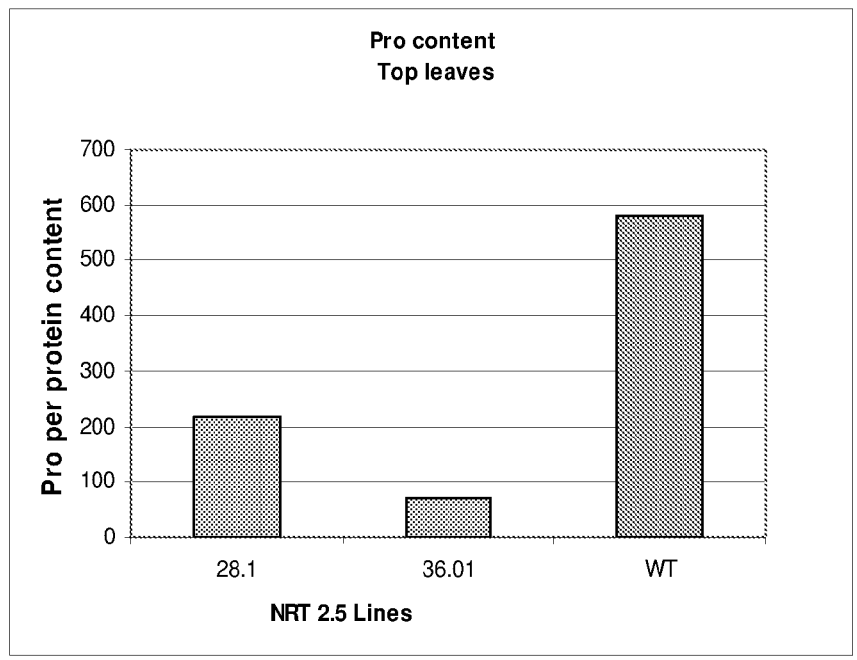
Figure 4A:
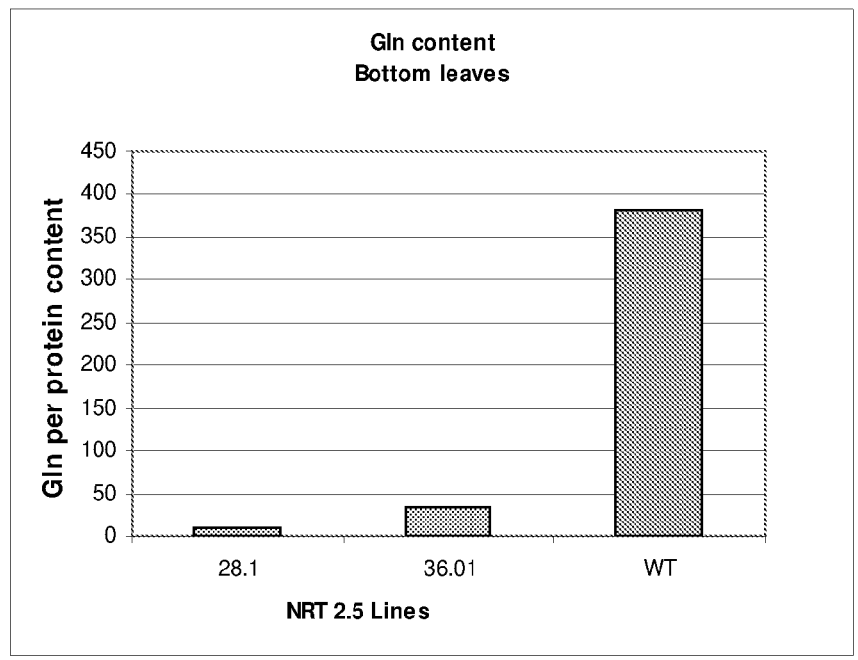
Figure 4B:
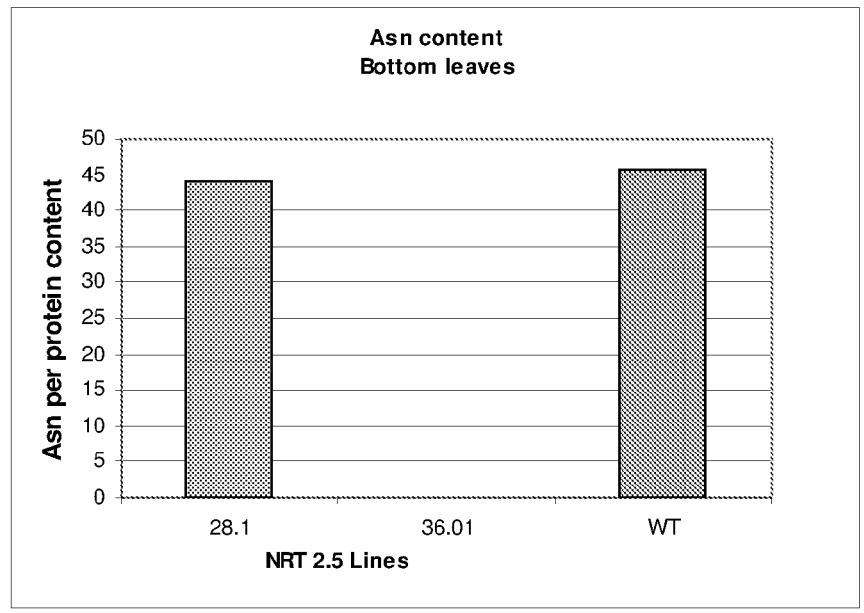
Figure 4C:
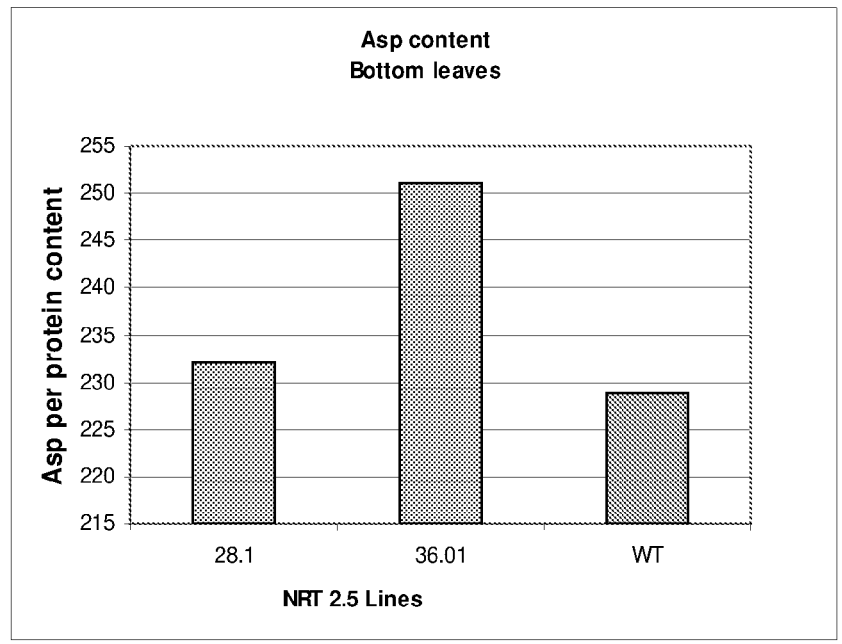
Figure 4D:
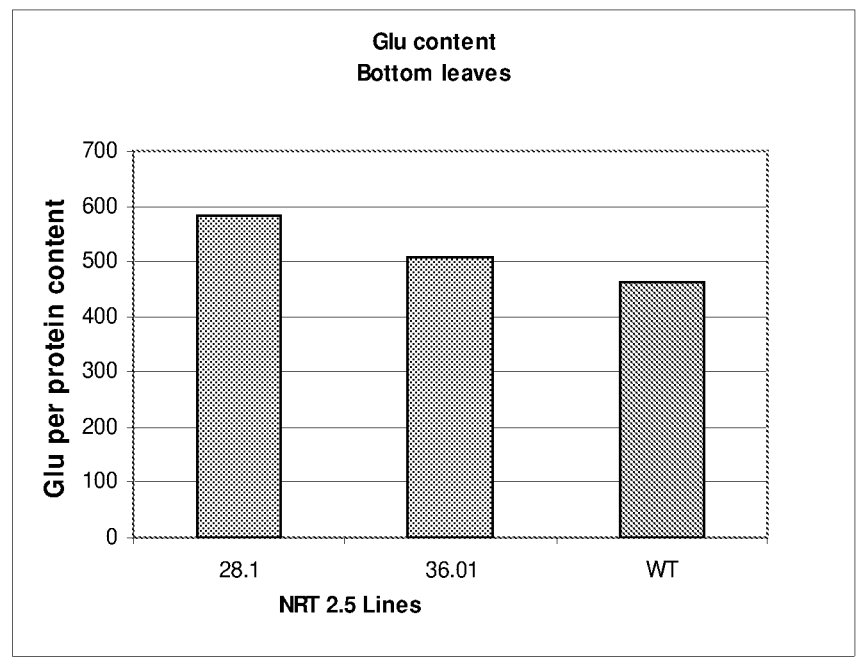
Figure 4E:
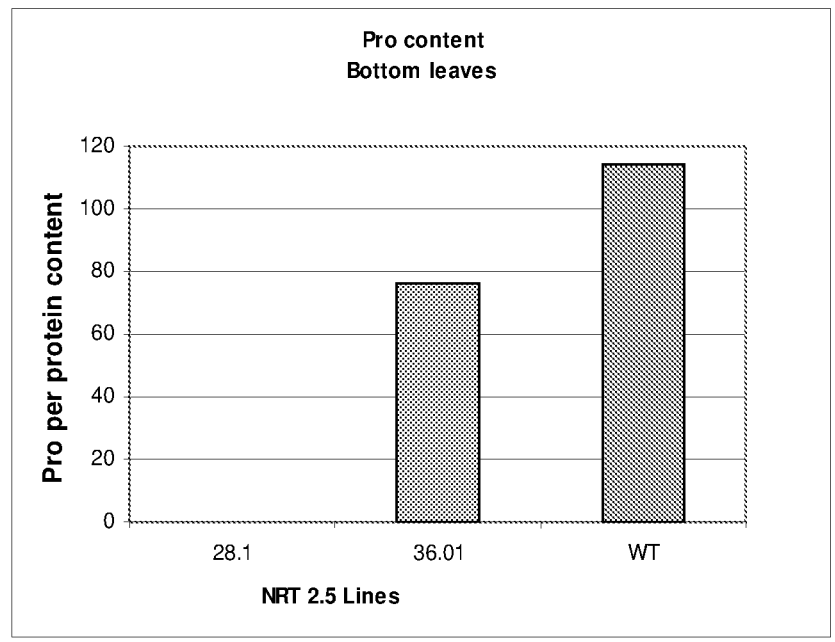

The inventors have developed a construct, as shown in FIG. 2, and two transgenic plant lines, referred to as 28.1 and 36.01, in which the concentration of nitrate and various amino acids (Gln, Asn, Asp, Glu, Pro) was significantly decreased upon expression of the nitrate transporter gene *Arabidopsis thaliana* nrt2.5 under the control of the constitutive promoter, Carnation Etched Ring Virus (CERV) promoter (Hull et al., 1986, EMBO J., 5, 3083-3090).

Example 1

Isolation of *Arabidopsis thaliana* Nitrate Transporter Gene

The *Arabidopsis thaliana* nitrate transporter gene used in these experiments was Atnrt2.5.

Design of Primers

The full length genomic sequence coding for the nitrate transporter 2.5 from *Arabidopsis thaliana* was identified (Accession Number for the sequence was: AT1G12940). Primers for use in PCR to isolate the genomic sequence were designed, which were tailed at the 5' end with a 4 bp spacer and suitable restriction sites. attB restriction sites were generated at the 5' and 3' end of the fragment to enable the cloning of the fragments into appropriate vectors.

It will be appreciated by the skilled person that other PCR primers could be designed incorporating the required features of the primers and alternative restriction enzyme sites.

Isolation of *Arabidopsis* Genomic DNA Encoding Nrt2.5

*Arabidopsis thaliana* var. Columbia genomic DNA was extracted from the rosette leaves of 3-week old plants using the Qiagen DNA Easy miniprep extraction kit. Briefly, genomic DNA was extracted from leaf samples using a QIAGEN DNeasy Plant DNA extraction kit (#69106) (QIAGEN Ltd., Crawley, UK), following the manufacturer's instructions. This method provided large amounts of very clean DNA suitable for gene isolation and cloning strategies. The principle of the kit utilises the specific absorption of DNA under high salt conditions to a silica-gel based membrane whilst contaminants such as proteins, carbohydrates, polyphenolics and other plant metabolites, are washed away.

Isolation of Nitrate Transporter DNA Fragments

The genomic sequence of *Arabidopsis* nrt2.5 is 1933 bp long (accession number AUG12940). Genomic *Arabidopsis* nrt2.5 was amplified with primer pairs SEQ ID NO. 5 and SEQ ID NO. 6 (as shown below), which generated attB restriction sites at the 5' end and attB restriction sites at the 3' end of the fragment.

Atnrt2.5 (Forward)
[SEQ ID NO. 5]
CAA GGA TCC ATG GAG GTC GAA GGC AAA GGA GGA GAA Atnrt2.5 (Reverse)
[SEQ ID NO. 6]
CAA GGT ACC TCA AGT TTG GGG ATG AGT C PCR Conditions Cycle program: 1 cycle of 98° C. for 30 seconds, followed by 30 cycles of 98° C. for 10 seconds, 59° C. for 30 seconds and 72° C. for 1 minute 30 seconds, this was followed by 1 cycle of 72° C. for 5 minutes. Bands were isolated using Advantage 2 polymerase (Clonetech) and following the manufacturer's instructions.

An aliquot of the PCR reaction was then analysed by agarose gel electrophoresis. Reactions were precipitated and then stored. Nitrate transporter DNA fragments were then cloned into pCR4-TOPO vectors (available from Invitrogen), as described below.

Ligation Reactions

1 µl of pCR4-TOPO was taken with 1 µl salt solution, and 4 µl PCR reaction. The mixture was left at room temperature for 20 mins. 2 µl of the ligation reaction mixture was then taken with TOP10 chemically competent *E. coli* cells, and then left on ice for 30 mins. The cells were heat-shocked at 42° C., and then left on ice for 2 mill. The cells were then incubated in 250 µl SOC medium at 37° C. for 90 minutes. The cells were then plated onto agar plates containing Kanamycin and left overnight at 37° C. Cells containing plasmids grew into colonies, for each gene sequence, and then 16 single colonies were picked and cultured in LB medium. DNA mini preps (Qiagen) were made for each individual colony and a restriction digest using BamHI/SspI and SacI/KpNI was used to determine if the gene had been incorporated into the pCR4-TOPO vector with successfully inserted genomic DNA fragments.

Sequence Analysis

The nitrate transporter DNA fragments present in a number of independent pCR4-TOPO clones were sequenced. Analysis of the sequence showed that the clones contained the nitrate transporter 2.5 gene.

Example 2

Construction of Vectors for Tobacco Transformation

Cloning of genomic DNA encoding Atnrt 2.5 into a pBNP CERV binary vector Plasmids containing the NRT 2.5 gene were digested with BamHI and KpnI (Promega) to isolate the NRT2.5 gene fragment, which was then cloned into pBNP binary vectors (pBNP-CERV-nosT), which had also been digested with BamHI/KpnI. Ligated vectors were subsequently used to transform into chemically competent *E. coli* cells. The pBNP vector is an in-house vector created from the pBNP binary vector (van Engelen et al., 1995, Transgenic Research, 4:288-290), containing the CERV promoter and the nopaline synthase terminator. It was converted into a Gateway ready vector by the addition of the Gateway conversion cassette (Invitrogen) following manufacturer's instructions. Cells containing the plasmid were selected on kanamycin plates. Clones were then isolated and the DNA was extracted and analysed by restriction digestion followed by sequencing.

The CERV promoter is a constitutive promoter of the caulimovirus group of plant viruses. It was isolated and characterised in 1986 by Hull et al. and is characteristic of CaMV (Hull et al., 1986), but has little sequence similarity with the CaMV 35S promoter.

The following binary vector was produced pGNP024 0096 001 (see FIG. 2): Carnation Etched Ring Virus (CERV) promoter: Nrt2.5 genomic: Nos terminator. The binary vector was then transformed into *Agrobacterium tumefaciens* LBA 4404 by electroporation. This was performed by mixing 40 µl of *A. tumefaciens* electrocompetent cells and 0.5 µg of plasmid DNA, and placing in a pre-cooled cuvette. The cells were then electroporated at 1.5 Volts, boo Ohms and 25 µFD. 1 ml of 2YT media was added to the cuvette and the mixture was decanted into a 30 ml universal container and incubated at 28° C. for 2 hours in a shaking incubator. 100 µl of cells were then plated onto kanamycin (50 µg/ml) and streptomycin (100 µg/ml) LB agar plates. The plates were left to incubate for 2 days at 28° C.

Example 3

Transformation of Tobacco

Burley PH2517 plants were transformed with pGNP024 0096 001 using the method of leaf disk co-cultivation, as described by Horsch et al. (Science 227: 1229-1231, 1985). The youngest two expanded leaves were taken from 7-week old tobacco plants and were surface-sterilised in 8% Domestos for 10 minutes and washed 3 times with sterile distilled water. Leaf disks were then cut using a number 6 cork borer and placed in the transformed *Agrobacterium* suspension for approximately two minutes. The discs were then gently blotted between two sheets of sterile filter paper. 10 disks were placed on MS 3% sucrose+2.2 µM BAP+NAA plates, which were then incubated for 2 days in the growth room. Discs were then transferred to plates of MS media+3% sucrose+2.2 µM BAP+0.27 µM NAA supplemented with 500 g/l Cefotaxime and 100 g/l kanamycin. The discs were transferred onto fresh plates of the above medium after 2 weeks. After a further two, weeks the leaf disks were transferred onto plates containing LS media+3% sucrose+ 0.5 µM BAP supplemented with 500 mg/l Cefotaxime and too mg/l kanamycin. The leaf disks were transferred onto fresh medium every two weeks. Shoots were excised as they appeared and transferred to jars of LS media+3% sucrose+ 0.5 µM BAP supplemented with 500 mg/l Cefotaxime. The shoots were transferred, in jars, to LS media+3% sucrose+ 250 mg/l Cefotaxime after approximately 3 weeks. After a further 3-4 weeks, the plants were finally transferred to LS media+3% sucrose (no antibiotics) and rooted. Once the plants were rooted they were transferred to soil in the greenhouse.

Example 4

Analysis of Transformed Plants for the Presence of the Atnrt2.5 Construct

Analysis of Regenerated Tobacco Transformants

Leaf material was taken from regenerated tobacco plants and genomic DNA was isolated. A leaf disc (approximately 30 mg) was excised from an in vitro grown plant and placed in a 1.5 ml Eppendorf tube. The tissue was homogenised using a micropestle and 400 µl extraction buffer (200 mM Tris HCL pH 8.0; 250 mM NaCl; 25 mM EDTA; 0.5% SDS; 40 µg/ml Rnase A) was added and ground again carefully to ensure thorough mixing. Samples were vortex-mixed for approximately 5 seconds and then centrifuged at 10,000 rpm for 5 minutes. A 3500 aliquot of the resulting supernatant was placed in a fresh Eppendorf tube and 3500 chloroform was added. After mixing, the sample was allowed to stand for 5 minutes. This was then centrifuged at 10,000 rpm for 5 minutes. A 300 µl aliquot of the supernatant was removed into a fresh Eppendorf tube. To this, 300 µl of propan-2-ol was added and mixed by inverting the Eppendorf several times. The sample was then allowed to stand for 10 minutes. The precipitated DNA was collected by centrifuging at 10,000 rpm for 10 minutes. The supernatant was discarded and the pellet air dried. The pellet of DNA was resuspended in 500 of distilled water and was used as a template in Q PCR. Burley PH2517 plants were analysed by Q-PCR to check for transgenic events.

QPCR analysis using the $\Delta\Delta C_t$ or Comparative $C_t$ method was carried out to calculate the copy number of the insertion at each generation of plants. At T0, plants with a single insertion were taken to seed to produce plants at T1 which segregate. The 2-copy homozygous lines were then selected all of which will then produce homozygous offspring. To carry out this procedure, genomic DNA was isolated from approximately 40 mg of tobacco leaf using the Qiagen DNA easy kit. 2.5 µl of this genomic DNA was then used in the following paired Hydrolysis probe PCR reactions.

Cyclophylin (Reference or house-keeping gene) and NPTII the marker gene inserted with the vector.

| Target | SEQ ID No: | Function | Sequence | Probe label | Probe Quencher |
|---|---|---|---|---|---|
| NPTII | 7 | Probe (anti-sense) | CAGAAAAGC GGCCATTTT CCACCA | Vic | TAMARA |
| NPTII | 8 | Primer | TGCCTGCTT GCCGAATATC | None | None |
| NPTII | 9 | Primer | CCGGCCACA GTCGATGA | None | None |
| Cyclo-philin | 10 | Probe | TCTACGGTG CCAAATTCG CCGA | FAM | TAMARA |
| Cyclo-philin | 11 | Primer | CTCAACCTT CCACCGTGT GAT | None | None |
| Cyclo-philin | 12 | Primer | ACCGGTGTG CTTCCTCTT GAA | None | None |

The reactions were set up in duplicate in a total of 25 µl on the ABI7900HT QPCR machine, with the following program—1 cycle 50 C 2 minutes, 1 cycle 95 C 10 minutes then 40 cycles or 95 C 15 seconds 60 C for 1 minute. This well-documented technique allows comparison of unknown copy number material to known calibrator lines (DNA of a known copy number) without the need for DNA quantification.

Results:
pGNP024 0096 001: Virginia/Burley 2 single copies

Example 5

Analysis of Transformed Plants for Nitrate Transporter Expression mRNA Levels Assayed by RT-PCR Total RNA was isolated from tobacco leaf discs using the Ambion RNAqueous kit (Ambion Inc., Canada). All frozen samples were ground under liquid nitrogen to a fine powder using a tissuelyser. Extracellular membranes, polysaccharides and high molecular weight DNA were precipitated by centrifugation at 13,000 rpm for 5 minutes at 4° C. The supernatant was transferred to the filter cartridge supplied with the kit and centrifugation used to wash and purify the RNA which was then eluted with elution buffer. RNA samples were stored at −80° C. until further use.

RT-PCR was performed on the total RNA using Invitrogen's 1-step RT-PCR superscript III. The resulting cDNA was then amplified with primers specific for Atnrt2.5 (SEQ ID No's: 13 and 14) to establish gene expression.

GTCTTAAGGATCCATGGAGGT [SEQ ID NO. 13]

TGCGATGATGTTGTCAATG [SEQ ID NO. 14]

The annealing temperature for the two RT-PCT primers was 59.1° C. Controls were carried out using RNA without the RT reaction to confirm there was no DNA contamination. Wild-type controls were run alongside transgenic lines and plasmid control to give correct band size.

Example 6

Analysis of "Upper" and "Lower" Tobacco Leaf Nitrate Content

Quantification of nitrate and/or nitrite levels in wild-type and transgenic Burley PH2517 plants was performed using HPLC. This method for determining nitrate concentrations in plant tissues is described in Sharma et al., 2008 (Malaria Journal, 7: pp71). HPLC provides highly accurate measurements of nitrate and/or nitrite levels from plant samples and also reduces the concerns associated with handling hazardous agents due to the increased level of automation associated with the methodology.

Materials are:
Running Buffer: 5 mM $K_2HPO_4$, 25 mM $KH_2PO_4$ at pH3
Extraction Buffer: 5 mM $K_2HPO_4$, 25 mM $KH_2PO_4$ at pH3

Method: Firstly, 2 ml of the phosphate buffer was added to 250-300 mg of ground leaf material and homogenised in mortar with a pestle. These ratios can be modified according to the expected level of nitrate. The homogenate was then centrifuged at 16000 rpm at +4° C. for 10 minutes. 1 ml of the supernatant was then filtered through a syringe filter (0.2 µm) into an HPLC vial. Nitrate and Nitrite standard curves were constructed with concentrations range of 0-1 mM for nitrate and 0 to 100 µM for nitrite. The injection volume is 20 µl.

The peak identification is done according to peak timing. Peak timing is variable depending on column age and a number of other factors. Thus standards should be used to assess peak position and related this to peak fun off time in samples.

The nitrate results illustrated in FIG. 5 show that there is a lowering of leaf nitrate concentration in the transformed plants with the CRV-AtNrt2.5 construct of the invention. Although they do not wish to be bound by theory, the inventors hypothesise that the AtNrt2.5 protein is acting as a nitrogen remobiliser. This results in the leaves being depleted of nitrate.

Example 7

Analysis of Tobacco "Upper" and "Lower" Leaf Amino Acid Content

As shown in Example 6 (FIG. 5), the inventors had established that the genetically modified test plant lines, 28.1 and 36.01, possess a significantly reduced concentration of nitrate within their upper and lower leaves, and enhanced nitrate remobilisation, compared to their wild-type counterparts. However, it is conceivable that this reduction in the nitrate content may have occurred due to an overall change in the distribution and management of nitrogen, and not just nitrate, within the plant. Several studies in Nitrogen Use Efficiency (NUE) indicate that modification of Glutamine (Gln) and Asparagine (Asn) levels correspond to the assimilation of nitrate (i.e. nitrogen) and its remobilization. Therefore, in order to determine whether the test plants exhibit a difference in their overall distribution of nitrogen, the amino acid content of wild-type and test plant leaves was measured.

The amino acid content of wild-type and transgenic Burley PH2517 plants was determined using the EZ: Faast LC/MS kit supplied by Phenomenex. All the reagents and the supplies, including the HPLC column, are components of the kit. All the steps of the procedure are provided in the User's manuals KH0-7338 which are used as a protocol.

Method: In principle, it involves solid phase extraction of the samples to be analysed, followed by a derivatization and a liquid/liquid extraction. The derivatized samples were analyzed quickly by liquid chromatography-mass spectrometry (LC-MS).

The solid phase extraction was performed via a sorbent packed tip that binds amino acids while allowing interfering compounds to flow through. Amino acids which were bound to the sorbent were then extruded into the sample vial and quickly derivatized with reagent at room temperature in aqueous solution. Derivatized amino acids concomitantly migrated to the organic layer for additional separation from interfering compounds. The organic layer was then removed, evaporated and re-dissolved in aqueous mobile phase and analyzed on a LC-MS system.

FIGS. 3A-E shows that the top leaves of both test plants lines over-expressing the Atnrt2.5 nitrate transporter, possess a reduced content of all the amino acids measured, compared to that within the top leaves of their wild-type counterpart. Therefore, this suggests that within the top leaves of the test plant, the amino acid content has been reduced by over-expression of the CRV-AtNrt2.5. In view of the reduced nitrate content of the test plant leaves, as shown in Example 6, and the reduced amino acid content of the upper leaves of the two plant lines, the inventors have concluded that there is reduced nitrate available for TSNA formation in the upper leaves of plants that over-express CRV-AtNrt2.5, which would clearly be advantageous.

FIGS. 4A-E show that the bottom leaves of the test plant lines posses variable concentrations of amino acids compared to their wild-type counterpart. Glutamine (FIG. 4A), Proline (FIG. 4E) and the Asparagine content of test plant line 36.01 (FIG. 4B) were the only amino acids which exhibited a reduced content compared to their wild-type counter part. Like the upper leaves, although less consistent, the reduced amino acid content of the lower leaves of the two plant lines and the reduced nitrate content of the lower leaves of the two plant lines (as shown in Example 6) has led the inventors to conclude that the there is reduced nitrate available for TSNA formation in the lower leaves of plants that over-express CRV-AtNrt2.5.

Example 8

Analysis of Tobacco "Middle" Leaf Nitrate Content in T2 Plants

Method: Quantification of nitrate and/or nitrite levels in wild-type and transgenic Burley PH2517 plants was performed using the method described in Example 6.

FIG. 6 shows that the middle leaves of both (T2) test plants lines over-expressing the Atnrt2.5 nitrate transporter, possess a reduced nitrate content, compared to the middle leaves of their wild-type counterpart. Therefore, this suggests that within the middle leaves of the test plant, the nitrate content has been reduced by over-expression of the CRV-AtNrt2.5.

As mentioned above (in Example 6), although not wishing to be bound by following theory, the inventors hypothesise that the AtNrt2.5 protein acts as a nitrogen remobiliser, which causes a reduction in the nitrate content of leaves.

Example 9

Analysis of Tobacco "Middle" Leaf Amino Acid Content in T2 Plants

The physiology of a leaf is dependent on its position in relation to the rest of the plant. Therefore, tobacco growers must bear this information in mind when considering what flavour a leaf may possess.

During flowering, a process called remobilization occurs, which results in the transport of nutrients, such as amino acids and nitrogenous compounds, out from the base of the plant towards the top of the plant. In addition, remobilized nutrients will be used as an energy source for seed production. Therefore, lower and upper leaves will have a different nitrogen content illustrated by a different amino acid profile. In view of the above, the inventors decided to measure the concentration of amino acids, which are believed to be involved in the nitrogen assimilation pathway, in the middle leaves of Burley plants.

Method: The amino acid content of the wild-type and transgenic Burley PH2517 plants was determined using the same method described in Example 7.

FIG. 7 summarises the effect of Atnrt2.5 nitrate transporter over-expression on the concentrations of Glu, Asp, Pro, Gln and Asn (i.e. amino acids believed to be involved in the nitrogen assimilation pathway of plants) in two plant lines, 28 and 48. This figure clearly shows that plants harbouring the Atnrt2.5 nitrate transporter construct exhibit a significant reduction (compared to the middle leaves of their wild-type counterpart) in the concentration of all the amino acids measured. In view of the reduced nitrate content of the test plant leaves, as shown in Examples 6 and 8, and the reduced amino acid content of the middle leaves of the two plant lines analysed, the inventors conclude that there is reduced nitrate available for TSNA formation in the leaves of plants that over-express CRV-AtNrt2.5, which would clearly be advantageous for tobacco plants. Furthermore, manipulation of the amino acid profiles can be used to modify the flavour of tobacco.

SUMMARY

The experiments described herein establish an interesting link between the knowledge that At NRT2.5 is regulated by nitrogen starvation (and has a role in the nitrate remobilisation) and the results, which show an increase of some amino acids which are recognized as markers for nitrogen remobilization. Studies in *Arabidopsis* and tobacco have shown that certain amino acids can be used as markers to determine remobilisation of nitrogen compounds (Diaz et al, 2005, Plant Physiology, 138: 898-908; and Masclaux et al 2000, Planta, 211:510-518). In particular the amino acids, glutamine (GLN) and asparagine (ASN), are the main amino acids that are translocated to the phloem for transport to sink tissues, i.e the reproductive organs and photosynthetically active regions of the plant. ASN and GLN are suggested as being signalling molecules by Seebauer et al, 2004 (Plant Physiology, 136 (4):4326-34), indicating that the plants are remobilising nitrogen sources for seed production. Diaz showed that, in *Arabidopsis*, ASN and aspartate (ASP) are good markers for senescence which is characterised also by lower levels of nitrate and nitrogen compounds in the plant. Masclaux also concluded that proline (PRO) in tobacco is reduced significantly in older senesced leaves that are undergoing remobilisation of nutrients.

SEQUENCE LISTING

<160> NUMBER OF SEQ ID NOS: 14

<210> SEQ ID NO 1
<211> LENGTH: 1933
<212> TYPE: DNA
<213> ORGANISM: Arabidopsis thaliana

<400> SEQUENCE: 1

| | | | | | | |
|---|---|---|---|---|---|---|
| atggaggtcg | aaggcaaagg | aggagaagct | ggaaccacca | ccacaaccgc | acctcggagg | 60 |
| ttcgcacttc | cggtggacgc | ggagaacaaa | gcaacaactt | tccgactatt | ctcagtcgct | 120 |
| aaacctcaca | tgagagcttt | ccatctctca | tggtttcaat | tcttttgctg | cttcgtctcc | 180 |
| actttcgcag | ctccgcctct | cctccctgtt | atccgtgaaa | atcttaacct | caccgccacc | 240 |
| gacatcggaa | acgccggaat | agcctctgtc | tccggcgctg | ttttcgctcg | tatcgtcatg | 300 |
| ggcacggcat | gtgatctttt | cggtccacgt | ctagcctccg | ccgctttgac | gctctccacc | 360 |
| gctcccgccg | tctatttcac | cgccgggata | aagtctccga | tcgggtttat | catggtgaga | 420 |
| ttcttcgccg | gattctctct | cgccactttc | gtctcgactc | agttctggat | gagctccatg | 480 |
| ttctctggac | ccgtcgtggg | ttcggctaac | ggaatcgccg | ccgggtgggg | taacctcgga | 540 |
| ggaggcgcga | cgcagctgat | catgcccatc | gtgttctcgt | tgattcgtaa | tatgggagcc | 600 |
| accaagttca | ccgcgtggag | gatcgctttt | ttcatcccg | gtctctttca | gactctctct | 660 |
| gctttcgccg | ttctcttgtt | cggtcaggta | acaaaccaat | cacactcacc | ggttcagtta | 720 |
| ttttggtttt | ttcaactaat | ccggttttga | gaatttatca | ccaagttatt | ttttgttttg | 780 |
| gttaaattta | ctttctttgt | atagccagtt | tatcctgttc | tatataaatg | attaaaccga | 840 |
| ttcgtttagg | tgcaaacccg | gtttattgat | accggtttgg | gtcgtctagt | agagtcttta | 900 |
| gtcggttaat | catggtcgag | tttcagtgga | tatggacaat | aactgtttaa | tcatctaagt | 960 |
| tgtgtctatt | acaaggaata | gtaaaaggat | acatttgttt | tgtcttatgt | ttgctatatg | 1020 |
| tttttggaaa | tgagtaggat | cttcctgatg | gagattattg | ggcgatgcat | aaatctggag | 1080 |
| agagggagaa | agatgatgtg | gggaaagtga | tatctaatgg | aatcaaaaac | tatagggat | 1140 |
| ggataacagc | attagcatat | ggctattgtt | ttggagtaga | gcttaccatt | gacaacatca | 1200 |
| tcgcagaata | tttcttcgat | agattccatt | taaagctcca | gacagcaggg | attatagcag | 1260 |
| cgagttttgg | actagccaat | ttttttcgcta | gacctggagg | aggaattttc | tctgatttta | 1320 |
| tgtcgagacg | gtttgggatg | agaggaaggt | tgtgggcttg | gtggattgtg | caaacatcag | 1380 |
| gaggtgtatt | atgcgcatgt | cttggccaga | tttcttcctt | gacagtgtct | ataattgtta | 1440 |
| tgcttgtctt | ctctgtattc | gtccaagccg | cttgtggact | tacctttggc | gttgttccct | 1500 |
| ttatttctag | aaggtaacat | acattttggt | attgagttgc | ttgattggtt | attcaacatt | 1560 |
| tttgcttaca | aaagtttgtt | tatgcagatc | tcttggggtg | gtatcgggaa | tgactggtgc | 1620 |
| gggaggcaat | gtaggcgcgg | tcttaacaca | gttgatattc | ttcaaaggat | cgacatacac | 1680 |
| gagagagacg | ggtataactc | taatgggggt | aatgtcaatc | gcatgttcat | taccaatatg | 1740 |
| cttgatttac | tttccgcaat | ggggaggtat | gttttgtgga | ccctcttcca | aaaaagcaac | 1800 |
| tgaagaagac | tattatctcg | ccgaatggaa | cgatgaagag | aaagaaaaga | acttacatat | 1860 |
| cggaagccaa | aaatttgcgg | aaaccagcat | tagcgaaaga | ggtcgagcca | caacgactca | 1920 |
| tccccaaaact | tga | | | | | 1933 |

```
<210> SEQ ID NO 2
<211> LENGTH: 1509
<212> TYPE: DNA
<213> ORGANISM: Arabidopsis thaliana

<400> SEQUENCE: 2
atggaggtcg aaggcaaagg aggagaagct ggaaccacca ccacaaccgc acctcggagg      60
ttcgcacttc cggtggacgc ggagaacaaa gcaacaactt ccgactatt ctcagtcgct      120 aaacctcaca tgagagcttt ccatctctca tggtttcaat tcttttgctg cttcgtctcc     180
actttcgcag ctccgcctct cctccctgtt atccgtgaaa atcttaacct caccgccacc     240
gacatcggaa acgccggaat agcctctgtc tccggcgctg ttttcgctcg tatcgtcatg     300
ggcacggcat gtgatctttt cggtccacgt ctagcctccg ccgctttgac gctctccacc     360
gctcccgccg tctatttcac cgccgggata aagtctccga tcgggtttat catggtgaga     420
ttcttcgccg gattctctct cgccactttc gtctcgactc agttctggat gagctccatg     480
ttctctggac ccgtcgtggg ttcggctaac ggaatcgccg ccgggtgggg taacctcgga     540
ggaggcgcga cgcagctgat catgcccatc gtgttctcgt tgattcgtaa tatgggagcc     600
accaagttca ccgcgtggag gatcgctttt ttcatcccg tctctttca gactctctct       660 gctttcgccg ttctcttgtt cggtcaggat cttcctgatg agattattg gcgatgcat        720 aaatctggag agagggagaa agatgatgtg gggaaagtga tatctaatgg aatcaaaaac     780 tatagggat ggataacagc attagcatat ggctattgtt ttggagtaga gcttaccatt      840
gacaacatca tcgcagaata tttcttcgat agattccatt taaagctcca gacagcaggg     900
attatagcag cgagttttgg actagccaat ttttcgcta gacctggagg aggaattttc       960
tctgatttta tgtcgagacg gtttgggatg agaggaaggt tgtgggcttg gtggattgtg    1020
caaacatcag gaggtgtatt atgcgcatgt cttggccaga tttcttcctt gacagtgtct    1080
ataattgtta tgcttgtctt ctctgtattc gtccaagccg cttgtggact tacctttggc    1140
gttgttccct ttatttctag aagatctctt ggggtggtat cgggaatgac tggtgcggga    1200
ggcaatgtag cgcgggtctt aacacagttg atattcttca aaggatcgac atacacgaga    1260
gagacgggta taactctaat gggggtaatg tcaatcgcat gttcattacc aatatgcttg    1320
atttactttc cgcaatgggg aggtatgttt tgtggaccct cttccaaaaa agtaactgaa    1380
gaagactatt atctcgccga atggaacgat gaagagaaag aaaagaactt acatatcgga    1440
agccaaaaat ttgcggaaac cagcattagc gaaagaggtc gagccacaac gactcatccc    1500
caaacttga                                                            1509

<210> SEQ ID NO 3
<211> LENGTH: 502
<212> TYPE: PRT
<213> ORGANISM: Arabidopsis thaliana

<400> SEQUENCE: 3

Met Glu Val Glu Gly Lys Gly Gly Glu Ala Gly Thr Thr Thr Thr Thr
1               5                   10                  15

Ala Pro Arg Arg Phe Ala Leu Pro Val Asp Ala Glu Asn Lys Ala Thr
            20                  25                  30

Thr Phe Arg Leu Phe Ser Val Ala Lys Pro His Met Arg Ala Phe His
        35                  40                  45

Leu Ser Trp Phe Gln Phe Cys Cys Phe Val Ser Thr Phe Ala Ala
    50                  55                  60
```

```
Pro Pro Leu Leu Pro Val Ile Arg Glu Asn Leu Asn Leu Thr Ala Thr
 65                  70                  75                  80

Asp Ile Gly Asn Ala Gly Ile Ala Ser Val Ser Gly Ala Val Phe Ala
                 85                  90                  95

Arg Ile Val Met Gly Thr Ala Cys Asp Leu Phe Gly Pro Arg Leu Ala
                100                 105                 110

Ser Ala Ala Leu Thr Leu Ser Thr Ala Pro Ala Val Tyr Phe Thr Ala
                115                 120                 125

Gly Ile Lys Ser Pro Ile Gly Phe Ile Met Val Arg Phe Phe Ala Gly
                130                 135                 140

Phe Ser Leu Ala Thr Phe Val Ser Thr Gln Phe Trp Met Ser Ser Met
145                 150                 155                 160

Phe Ser Gly Pro Val Val Gly Ser Ala Asn Gly Ile Ala Ala Gly Trp
                165                 170                 175

Gly Asn Leu Gly Gly Gly Ala Thr Gln Leu Ile Met Pro Ile Val Phe
                180                 185                 190

Ser Leu Ile Arg Asn Met Gly Ala Thr Lys Phe Thr Ala Trp Arg Ile
                195                 200                 205

Ala Phe Phe Ile Pro Gly Leu Phe Gln Thr Leu Ser Ala Phe Ala Val
210                 215                 220

Leu Leu Phe Gly Gln Asp Leu Pro Asp Gly Asp Tyr Trp Ala Met His
225                 230                 235                 240

Lys Ser Gly Glu Arg Glu Lys Asp Asp Val Gly Lys Val Ile Ser Asn
                245                 250                 255

Gly Ile Lys Asn Tyr Arg Gly Trp Ile Thr Ala Leu Ala Tyr Gly Tyr
                260                 265                 270

Cys Phe Gly Val Glu Leu Thr Ile Asp Asn Ile Ile Ala Glu Tyr Phe
                275                 280                 285

Phe Asp Arg Phe His Leu Lys Leu Gln Thr Ala Gly Ile Ile Ala Ala
                290                 295                 300

Ser Phe Gly Leu Ala Asn Phe Phe Ala Arg Pro Gly Gly Gly Ile Phe
305                 310                 315                 320

Ser Asp Phe Met Ser Arg Arg Phe Gly Met Arg Gly Arg Leu Trp Ala
                325                 330                 335

Trp Trp Ile Val Gln Thr Ser Gly Gly Val Leu Cys Ala Cys Leu Gly
                340                 345                 350

Gln Ile Ser Ser Leu Thr Val Ser Ile Val Met Leu Val Phe Ser
                355                 360                 365

Val Phe Val Gln Ala Ala Cys Gly Leu Thr Phe Gly Val Val Pro Phe
                370                 375                 380

Ile Ser Arg Arg Ser Leu Gly Val Val Ser Gly Met Thr Gly Ala Gly
385                 390                 395                 400

Gly Asn Val Gly Ala Val Leu Thr Gln Leu Ile Phe Phe Lys Gly Ser
                405                 410                 415

Thr Tyr Thr Arg Glu Thr Gly Ile Thr Leu Met Gly Val Met Ser Ile
                420                 425                 430

Ala Cys Ser Leu Pro Ile Cys Leu Ile Tyr Phe Pro Gln Trp Gly Gly
                435                 440                 445

Met Phe Cys Gly Pro Ser Ser Lys Lys Val Thr Glu Glu Asp Tyr Tyr
                450                 455                 460

Leu Ala Glu Trp Asn Asp Glu Glu Lys Glu Lys Asn Leu His Ile Gly
465                 470                 475                 480
```

Ser Gln Lys Phe Ala Glu Thr Ser Ile Ser Glu Arg Gly Arg Ala Thr
            485                 490                 495

Thr Thr His Pro Gln Thr
            500

<210> SEQ ID NO 4
<211> LENGTH: 232
<212> TYPE: DNA
<213> ORGANISM: Carnation etched ring virus

<400> SEQUENCE: 4
agcttgcatg cctgcaggtc gagcttttag gattccatag tgataagata tgttcttatc      60
taaacaaaaa agcagcgtcg gcaaaccata cagctgtcca caaaaaggaa aggctgtaat     120
aacaagcgga cccagcttct cagtggaaga tactttatca gacactgaat aatggatgga     180
ccctaccacg attaaagagg agcgtctgtc taaagtaaag tagagcgtct tt             232

<210> SEQ ID NO 5
<211> LENGTH: 36
<212> TYPE: DNA
<213> ORGANISM: Arabidopsis thaliana

<400> SEQUENCE: 5
caaggatcca tggaggtcga aggcaaagga ggagaa                                36

<210> SEQ ID NO 6
<211> LENGTH: 28
<212> TYPE: DNA
<213> ORGANISM: Arabidopsis thaliana

<400> SEQUENCE: 6
caaggtacct caagtttggg gatgagtc                                         28

<210> SEQ ID NO 7
<211> LENGTH: 24
<212> TYPE: DNA
<213> ORGANISM: Arabidopsis thaliana

<400> SEQUENCE: 7
cagaaaagcg gccattttcc acca                                             24

<210> SEQ ID NO 8
<211> LENGTH: 19
<212> TYPE: DNA
<213> ORGANISM: Arabidopsis thaliana

<400> SEQUENCE: 8
tgcctgcttg ccgaatatc                                                   19

<210> SEQ ID NO 9
<211> LENGTH: 17
<212> TYPE: DNA
<213> ORGANISM: Arabidopsis thaliana

<400> SEQUENCE: 9
ccggccacag tcgatga                                                     17

<210> SEQ ID NO 10
<211> LENGTH: 22
<212> TYPE: DNA
<213> ORGANISM: Arabidopsis thaliana

```
<400> SEQUENCE: 10
tctacggtgc caaattcgcc ga                                              22

<210> SEQ ID NO 11
<211> LENGTH: 21
<212> TYPE: DNA
<213> ORGANISM: Arabidopsis thaliana

<400> SEQUENCE: 11
ctcaaccttc caccgtgtga t                                               21

<210> SEQ ID NO 12
<211> LENGTH: 21
<212> TYPE: DNA
<213> ORGANISM: Arabidopsis thaliana

<400> SEQUENCE: 12
accggtgtgc ttcctcttga a                                               21

<210> SEQ ID NO 13
<211> LENGTH: 21
<212> TYPE: DNA
<213> ORGANISM: Arabidopsis thaliana

<400> SEQUENCE: 13
gtcttaagga tccatggagg t                                               21

<210> SEQ ID NO 14
<211> LENGTH: 19
<212> TYPE: DNA
<213> ORGANISM: Arabidopsis thaliana

<400> SEQUENCE: 14
tgcgatgatg ttgtcaatg                                                  19
```

The invention claimed is:

1. A method of decreasing nitrate concentration in leaves of a test tobacco plant to below that of the corresponding nitrate concentration in leaves of a wild-type tobacco plant cultured under the same conditions, the method comprising:
   (i) transforming a plant cell of a test tobacco plant with a genetic construct, or a vector comprising said genetic construct, the construct comprising a promoter operably linked to a coding sequence encoding a polypeptide having nitrate transporter activity, wherein the polypeptide comprises the amino acid sequence as set out in SEQ ID No.3, or an amino acid sequence which has at least 95% sequence identity therewith, wherein the promoter is a Carnation Etched Ring Vims (CERV) promoter; and
   (ii) regenerating a tobacco plant from the transformed cell, wherein the regenerated transformed tobacco plant expresses said construct and has decreased nitrate concentration in its leaves when compared to the wild-type tobacco plant.

2. A method of producing a transgenic tobacco plant which transports nitrate out of a leaf at a higher rate than a corresponding wild-type tobacco plant cultured under the same conditions, the method comprising:
   (i) transforming a plant cell of the wild-type tobacco plant with a genetic construct, or a vector comprising said genetic construct, the construct comprising a promoter operably linked to a coding sequence encoding a polypeptide having nitrate transporter activity, wherein the polypeptide comprises the amino acid sequence as set out in SEQ ID No.3, or an amino acid sequence which has at least 95% sequence identity therewith, wherein the promoter is a Carnation Etched Ring Virus (CERV) promoter and
   (ii) regenerating a tobacco plant from the transformed cell, wherein the regenerated transformed tobacco plant expresses said construct and has decreased nitrate concentration in its leaves when compared to the wild-type tobacco plant.

3. The method according to claim 1, wherein the coding sequence comprises a nucleic acid sequence as set out in either SEQ ID No.1 or SEQ ID No.2, or a polynucleotide sequence which has at least 95% sequence identity therewith.

4. The method according to claim 1, wherein the promoter is a Carnation Etched Ring Virus (CERV) promoter and comprises the nucleotide sequence as set out in SEQ ID No.4.

5. A transgenic tobacco plant comprising and expressing a genetic construct, or a vector comprising said genetic construct, the construct comprising a promoter operably linked to a coding sequence encoding a polypeptide having nitrate transporter activity, wherein the polypeptide comprises the amino acid sequence as set out in SEQ ID No.3, or an amino acid sequence which has at least 95% sequence identity therewith, wherein the promoter is a Carnation Etched Ring Virus (CERV) promoter, and wherein nitrate concentration in the leaves of the transgenic tobacco plant is reduced compared to nitrate concentration in the leaves of an unmodified tobacco plant.

6. A plant propagation product obtained from the transgenic tobacco plant according to claim 5 and which comprises and expresses the genetic construct, or the vector comprising said genetic construct, wherein the construct comprises a promoter operably linked to a coding sequence encoding a polypeptide haying nitrate transporter activity, wherein the polypeptide comprises amino acid sequence as set out in SEQ ID NO.3, or an amino acid sequence which has at least 95% sequence identity therewith, and wherein the promoter is a Carnation Etched Ring Virus (CERV) promoter.

7. A harvested tobacco leaf containing a lower level of nitrate than the corresponding level of nitrate in a harvested leaf taken from a wild-type tobacco plant cultured under the same conditions, wherein the leaf is harvested from the transgenic tobacco plant according to claim 5.

8. A method of modulating a profile of amino acids involved in the nitrogen assimilation of leaves of a test tobacco plant compared to the amino acid profile of corresponding leaves of a wild-type tobacco plant cultured under the same conditions, the method comprising:
(i) transforming a plant cell of the test tobacco plant with a genetic construct, or a vector comprising said genetic construct, the construct comprising a promoter operably linked to a coding sequence encoding a polypeptide having nitrate transporter activity, wherein the polypeptide comprises the amino acid sequence as set out in SEQ ID No.3, or an amino acid sequence which has at least 95% sequence identity therewith, wherein the promoter is a Carnation Etched Ring Virus (CERV) promoter; and
(ii) regenerating a tobacco plant from the transformed cell, wherein the regenerated transformed tobacco plant expresses the construct, and the profile of amino acids involved in the nitrogen assimilation of leaves of the regenerated transformed tobacco plant is modulated compared to the amino acid profile of corresponding leaves of the wild-type tobacco plant.

9. The method according to claim 8, wherein amino acids involved in the nitrogen assimilation pathway of plants and their leaves comprise glutamine (Gln), asparagine (Asn), aspartic acid (Asp), glutamic acid (Glu) or proline (Pro).

10. The method according to claim 8, wherein the construct decreases the concentration of the amino acids Pro and Gln in the lower leaves of a transgenic tobacco plant compared to corresponding leaves that are found in a wild-type tobacco plant grown under the same conditions.

* * * * *